US006800279B2

(12) United States Patent
Bernier et al.

(10) Patent No.: US 6,800,279 B2
(45) Date of Patent: Oct. 5, 2004

(54) CHEMICAL COMPOSITION THAT ATTRACT ARTHROPODS

(75) Inventors: Ulrich R. Bernier, Gainesville, FL (US); Donald R. Barnard, Gainesville, FL (US); Matthew M. Booth, Gainesville, FL (US); Daniel L. Kline, Gainesville, FL (US); Kenneth H. Posey, Gainesville, FL (US); Richard A. Yost, Gainesville, FL (US)

(73) Assignees: The United States of America as represented by the Secretary of the Agriculture, Washington, DC (US); University of Florida, Gainesville, FL (US)

( * ) Notice: Subject to any disclaimer, the term of this patent is extended or adjusted under 35 U.S.C. 154(b) by 0 days.

(21) Appl. No.: 09/848,236

(22) Filed: May 4, 2001

(65) Prior Publication Data

US 2002/0028191 A1 Mar. 7, 2002

Related U.S. Application Data

(62) Division of application No. 09/304,362, filed on May 4, 1999, now Pat. No. 6,267,953.

(51) Int. Cl.[7] .................... A01N 25/00; A01N 31/00; A01N 35/00; A01N 37/00
(52) U.S. Cl. .................... 424/84; 514/557; 514/675; 514/706; 514/724
(58) Field of Search .................... 424/84, 405, 537; 514/557, 675, 706, 724, 553, 579, 699, 700, 707, 703, 715, 727, 731, 739, 743, 762, 763, 764; 372/45–50; 257/13, 16, 96, 15, 17, 22, 94, 184, 190

(56) References Cited

U.S. PATENT DOCUMENTS

| | | | |
|---|---|---|---|
| 4,166,112 A | 8/1979 | Goldberg | 424/93 |
| 4,187,200 A | 2/1980 | Jenkin | 252/472 |
| 4,818,526 A | 4/1989 | Wilson et al. | 424/84 |
| 4,907,366 A | 3/1990 | Balfour | 43/132.1 |
| 5,657,756 A | 8/1997 | Vrba et al. | 128/653.1 |
| 5,679,364 A | 10/1997 | Levy | 424/405 |
| 5,943,815 A * | 8/1999 | Paganessi et al. | 43/107 |

OTHER PUBLICATIONS

STN/CAS online, file CROPU, Acc. No. 1998–89883 (Kline et al., J. Am. Mosq. Control Assoc. vol. 14, No. 3, pp. 289–297 (1998)), Abstract.*
Seitz, Microbial and Enzyme–Induced Flavors in Dairy Foods, J. Dairy Sci., vol. 73, pp. 3664–3691 (1990).*
Acree Jr., F., et al., "L–Lactic Acid: A Monquito Attractant Isolated from Humans", Science. 161, 1346–1347, (Sep. 2, 1968).
Bar–Zeev, M., et al., "Studies on the Attraction of Aedes Aegypti (Diptera: Culicidae) to Man", Journal of Medical Entomology, 14(1), 113–120, (Aug. 20, 1977).
Bernier, J.R., "Mass Spectrometric Investigation of Mosquito Attraction to Human Skin Emanations ", Ph. D. Thesis presented at the University of Florida, Published by UMI Dissertation Services, Ann Arbor, MI, 1–333 p., (1995).
Bernier, J.R., et al., "Analysis of Human Skin Emanations by Gas Chromatography/Mass Spectrometry. 1. Thermal Desorption of Attractants for the Yellow Fever Mosquito (Aedes aegypti) from Handled Glass Beads", Analytical Chemistry, 71 (1), Accelerated Articles, 1–7 p., (Jan. 1, 1999).
Bowen, M.F., et al., "Lactic Acid Sensitive Receptors in the Autogenous Mosquito Aedes atropalpus", Journal of Insect Physiology. 40 (7), 611–615, (1994).
Braks, M.A., et al., "Incubated Human Sweat But Not Fresh Sweat Attracts the Malaria Mosquito Anopheles gambiae Sensu Stricto", Journal of Chemical Ecology. 25 (3), 663–672, (1999).
Carlson, D.A., et al., "Carbon Dioxide Released from Human skin: Effect of Temperature and Insect Repellents", Journal of Medical Entomology, 29 (2), 165–170, (1992).
Carlson, D.A., et al., "Yellowfever Mosquitoes: Compounds Related to Lactic Acid that Attract Females", Journal of Economic Entomology. 66 (2), 329–331, (Apr. 1973).
Charlwood, J.D., et al., "Mosquito–Mediated Attraction of Female European but not African Mosquitoes to Hosts", Annals of Tropical Medicine and Parasitology, 89 (3), 327–329, (1995).
Davis, E.E., "Development of Lactic Acid–Receptor Sensitivity and Host–Seeking Behaviour in Newly Emerged Female Aedes Aegypti Mosquitoes", Journal of Insect Physiology, 30 (3), 211–215, (1984).
Davis, E.E., "Structure–Response Relationship of the Lactic Acid–Excited Neurones in the Antennal Grooved–Peg Sensilla of the Mosquito Aedes Aegypti", Journal of Insect Physiology, 34 (6), Printed in Great Britain, 443–449, (1988).
De Jong, R., et al., "Olfactory Responses of Host–Seeking Anopheles gambiae s.s. Giles (Diptera: Culicidae)", Acta Tropica, 59, 333–335, (1995).
De Jong, R., et al., "Selection of Biting Sites on Man by Two Malaria Mosquito Species", Experentia 51, 80–84, (1995).
Eiras, A.E., et al., et al., "Host Location by Aedeu aegypti (Diptera: Culicidae) : a Wind Tunnel Study of Chemical Cues", Bulletin of Entomological Research. 81, 151–160, (1991).
Eiras, A. E., et al., "Responeses of Female Aedes aegypti (Diptera: Culicidae) to Host Odours and Convection Current Using Currents Using an Olfactometer Bioassay", Bulletin of Entomological Research, 84, 207–211, (1994).

(List continued on next page.)

Primary Examiner—Thurman K. Page
Assistant Examiner—Frank Choi
(74) Attorney, Agent, or Firm—John D. Fado; Gail E. Poulos

(57) ABSTRACT

Compositions and methods employing the compositions for attracting arthropods. The compositions comprise at least one compound of formula I and at least one compound from group II.

12 Claims, No Drawings

OTHER PUBLICATIONS

Geier, M., et al., "A search for Components in Human Body Odour that Attract Females of Aedes Aegypti", *Ciba Foundation Symposium 200 on Olfaction in Mosquito–Host Interactions*, 132–148, (1996.

Gilles, M.T., "The Role of Carbon Dioxide in Host–Finding by Mosquitoes Diptera: Culicidae) a review", *Bulletin of Entomological Research*, 70 (1), 525–532, (Mar. 1980).

Guock, H.K., et al., "Responses of Mosquitoes and Stable Flies to a Man in a Light–Weight Rubber Diving Suit", *Journal of Economic Entomology*, 55 (3), 386–392, (1962).

Ikeshoji, T., "Synergistic Effect of Lactic Acid with a Chemosterilant Metepa to the Sound–Attracted Male Mosquito", *Jpn. Sanit, Zool.*, 38 (4), 333–338 (1987).

Kline, D.L., "Olfactory Responses and Field Attraction of Mosquitoes to Volatiles from Limburger Cheese and Human Foot Odor", *Journal of Vector Ecology.* 23 (2), 186–194, (Dec. 1998).

Kline, D.L., et al., "Field Studies on the Potential of Butanone, Carbon Dioxide, Honey Extract, 1–octen–3–ol, L–Lactic Acid and Phenols as Attractants for Mosquitoes", *Medical and Veterinary Entonology* 4, 383–391, (1990).

Knols, B.G., et al., "Behavioural and Electrophysiological Responses of the Female Malaria Mosquito Anopheles gambiae (Daptera: Culicidae) to Limburger Cheese Volatiles", *Bulletin of Entomological Research,* 87, 151–159, (1997).

Knols, B.G., et al., "Limburger Cheese as an Atrractant for the Malaria Mosquito Anopheles gambiae s.s.", *Parasitology Today,* 12 (4), 159–161, (1996).

Mboera, L.E., et al., "Olfactory Responses of Female Culex quinquefasciatus Say (Diptera: Culicidae) in a Dual–Choice Olfactometer", *Journal of Vactor Ecology,* 23 (2), 107–113, (Dec. 1998).

McCall, P.J., et al., "Attraction and Trapping of Aedes aegypti (Diptera: Culicidae) with Host Odors in the Laboratory", *Journal of Medical Entomology 33 (1),* 177–179, (1996).

Posey, K.H., et al., "Triple Cage Olfactometer for Evaluating Mosquito (Diptera: Culicidae) Attraction Responese", *Journal of Medical Entomology,* 35 (3), 330–334, (1998).

Price, G.D., et al., "The Attraction of Female Mosquitoes (Anopheles quadrimaculatus SAY) to Stored Human Emanations in Conjunction with Adjusted Levels of Relative Humidity, Temperature, and Carbon Dioxide", *Journal of Chemical Ecoology,* 5 (3), 383–395, (1979).

Rudolfs, W., "Chemotropism of Mosquitoes", *New Jersey Agricultural Experiment Stations, Bulletin 367*, New Brunswick, NJ, 1–23 p., (Mar. 1922).

Schreck, C. E., et al., "A Material Isolated from Human Hands that Attracts Female Monquitoes", *Journal of Chemical Ecology,* 8(2), 429–438, (1981).

Schreck, C.E., et al., "Mosquito Attraction to Substances from the Skin of Different Humans", *Journal of the American Mosquito Control Association* & (3), 406–410, (Sep. 1990).

Takken, W., "The Role of Olfaction in Host–Seeking of Mosquitoes: A Review", *Insect Sci. Applic.,* 12 (1/2/3), 187–294, (1991).

Takken, W., et al., "Carbon Dioxide and 1octen–3–OL as Mosquito Attractants", *Journal of the American Mosquito Control Association 5* (3), 311–316, (Sep. 1989).

Takken, W., et al., "Odor–Mediated Behavior of Afrotropical Malaria Mosquitoes", *Annu. Rev. Entomol., 44*, 131–157, (1999).

Takken, W., et al., "Odor–Mediated Flight Behavior of Anopheles gambiae Giles Sensu Stricto and An. stephensi Liston in Response to Carbon, Dioxide, Acetone, and 1–Octen–3–ol (Diptera: Culicidae)", *Journal of Insect Behavior 10* (3), 395–407, (May 1997).

Vale, G.A., et al., "The Use of 1–octen–3–ol, Acetone, and Carbon Dioxide to Improve Baits fot Taetse Flies, Glossina spp (Diptera; Glossinidae)", *Bull. ant. Res., 75,* 219–231, (1985).

Van Essen, P.H., et al., "Differential Responses of Aedes and Culex Mosquitoes to Octenol or Light in Combination with Carbon Dioxide in Queensland, Australia", *Medical and Veterinary Entomology,* 63–67, (1993).

Wensler, R.J., "The Effect of Odors on the Behavior of Adult Aedes aegypti and Some Factor Limiting Responsivesness", *Can, J. Zool., 50,* 415–420, (1972).

Willis, E. R., et al., "Reactions of Aedes Aegypti (L.) to Carbon Dioxide", *J. Exp. Zool., 121,* 149–179, (1952).

Saini et al., "A Behavioural Bioassay to Identify Attractive Odours for Glossinidae", (Medical and Veterinary Entomology, (1987), vol. 1, No. 3, pp. 313–318), STN/CAS online, file Medline, Abstract.

Mihok et al., "Trials of Traps and Attractants for Stomoxys spp. Diptera: Muscidae", (Journal of Medical Entomology, (1995) vol. 32, No. 3, pp. 283–289). STM/CAS online, file BIOSIS, Abstract.

Voskamp et al., "Olfactory Responses to Attractants and Repellants in Tsetse", (Medical and Veterinary Entomology, (1999) vol. 13, No. 4, pp. 386–392), STN/CAS online, file BIOSIS, Abstract.

Laye et al., "Chemical, Microbiological and Sensory Properties of Plain Nonfat Yogurt", (1993), (Journal of Food Science, vol. 58, No. 5, pp. 991–995).

Granata et al., "Improved Acid, Flavor and Volatile Compound Production in a High Protein and Fiber Soymilk Yogurt–like Product", (1996), (Journal of Food Science, vol. 61, No. 2, pp. 331–336.).

Hosono et al., "Metabolism of Brevibacterium Linens and Its Application." (Rakuno Kagaku No Kenkyu (1969), vol. 18, No. 6, pp. A164–A169), STN/CAS online, file CAPLUS, Abstract.).

Hansen et al., "Flavour of Sourdough Rye Bread Crumb", (1989), Lebensm.–Wiss.u.–Technol . . . , Bol. 22, pp. 141–144.).

Smith et al., (L–lactic Acid as a Factor in the Attraction of Aedes Aegyptic (Diptera: Culicidae) to Human Hosts, Ann. Entomol. Soc. Amer. (1970), vol. 63, No. 3, pp. 760–770.).

\* cited by examiner

US 6,800,279 B2

CHEMICAL COMPOSITION THAT ATTRACT ARTHROPODS

This is a divisional of application Ser. No. 09/304,362 filed May 4, 1999, now U.S. Pat. 6,267,953 which is herein incorporated by reference in its entirety.

BACKGROUND OF THE INVENTION

Insects have plagued people throughout history. Fast intercontinental travel and trade have enabled the importation of nonindigenous insect pests (e.g., species of mosquitoes, such as *Aedes albopictus*, the Asian Tiger mosquito) into the United States. As a result, the U.S. must face the task of controlling numerous species of nuisance pests, such as arthropods and, more specifically, mosquitoes. Some of these insects spread disease and, thus, are of great medical and veterinary importance. Control of these pests is necessary to reduce or eliminate the spread of arthropod-borne diseases.

The primary focus of this invention is the control or reduction of the population of mosquitoes. At least three "generations" of control methods have been developed over the years. The first generation of control methods comprise chemicals dispensed by foggers or sprayers, both on the ground and through the air. These chemicals may be classified as either adulticides or larvicides and are intended to attack and kill the adult mosquito or its larva, respectively. These chemicals usually have an inherent toxicity, which is potentially injurious to the environment, to marine life and wildlife, and ultimately to humans. As a result, these chemical insecticides have become viewed with disfavor.

One such insecticide product was "DURSBAN™ 10CR" produced by Dow Chemical Company in the mid-1970's. There were at least two problems with this product. First, it was inherently toxic and potentially harmful to the environment. Second, because of rapid turnover of the mosquito population and the selection of resistant genes by Dursban, insects could develop a resistance to the chemicals. Mosquitoes ultimately develop an immunity to adulticides of the same chemical family. This situation is referred to as "cross resistance" and illustrates that under adverse conditions, insects may adapt. This ability to adapt, often within a few generations, provides complications for researchers engaged in the field of pest control.

As a departure from the chemical adulticides and larvicides, a second generation of mosquito control product was developed. This second generation is known as insect growth regulators. Their purpose is to prevent the immature insect from transforming into an adult. This class of mosquito control product allows the larva to enter into its pupa stage but prevent the pupa from developing into an adult. These products have very low toxicity, or practically no toxicity, and hence are not detrimental to aquatic life. Due to the general application of this control material to the environment through a form such as a charcoal briquet, the products are messy, inconvenient to handle, and are very expensive. These products also require adequate surveillance of standing water and delivery of briquets to these locations. The potential exists that some sites will go untreated.

Over the past fifteen years, a third generation of insecticides has been developed. These are bacteriological methods for spreading endotoxins among insect populations. One of the most successful endotoxin agents used against insects is *Bacillus thuringiensis* Berliner var. *kurstaki*, a bacterium which infects the larvae of Lepidoptera (moths) that are to be destroyed. More recently, a new variety has been uncovered for use against mosquito and black fly larvae. This is *Bacillus thuringiensis* Berliner var. *israelensis* and its accompanying proteinaceous parasporal particles which contain protoxin. When a larvicidal microorganism of the bacillus type is used and is sprayed on the water in the form of a liquid produced by diluting the wettable powder or liquid concentrate with water, a similar problem is encountered. The bacillus spores and protoxin particles are heavier than water and sink. Additionally, the application of the bacillus does not have a sustained release—it is essentially "one shot"—and hence re-applications are often necessary to insure an effective mosquito control program. This is time consuming and expensive, and extensive surveillance is needed to target all breeding areas.

Besides these existing chemical and microbial insecticides, other devices and methods are known for the control or destruction of mosquitos and other aquatic pests.

U.S. Pat. Nos. 4,166,112 and 4,187,200, issued to Goldberg in 1979 and 1980, respectively, disclosed *Bacillus thuringiensis* in which a carrier was formulated as a buoyant colloidal suspension which stabilized just under the surface of the water.

According to information published by Biochem Products, a division of Salsbury Laboratories, Inc., a member of the Solvay Group, the earliest documented record of *Bacillus thuringiensis* was in Japan in 1901. In the decades since, at least 14 varieties of *B.t.* have been identified from several countries on the bases of biochemical characteristics and serotyping of vegetative cell flagellar antigens. *Bacillus thuringiensis*, Berliner also known as HD-1, Serotype H-3a3b, or *B.t.* variety *kurstaki*, has been registered in the United States since 1961 for control of Lepidopteran larvae or caterpillars and is the type commonly used in forestry, agriculture, home and commercial gardening and horticulture. Products containing *B.t.* reportedly have an excellent safety record with no documented incidents of serious or undesirable side effects on man and the environment. Biochem Products supplies a wettable powder or a flowable concentrate under the trademark "BACTIMOS™" which is derived from *B.t.i.*, Serotype H-14, *Bacillus thuringiensis* variety *israelensis*, and was discovered in Israel in 1976. This is a larvicidal microorganism comprising *Bacillus thuringiensis* Berliner var. *israelensis* and its accompanying proteinaceous parasporal particles which contain protoxin (commonly referred to as "*B.t.i.*").

For mosquito control purposes, the BACTIMOS™ (*B.t.i.*) is invariably mixed with water and is applied to large areas, using airplanes or helicopters. This method of application has been continually used despite the constant and critical need for an alternate delivery system for the myriad of ponds and other small bodies of water, as recognized in MOSQUITO NEWS in 1948.

Moreover, any attempt to impregnate *B.t.i.* (or the larvicidal microorganism of the aforesaid Goldberg patents) into the floating thermoplastic carrier of the aforesaid Cardarelli patent, would be impractical (if not impossible) and would destroy the stated utility of these references. An exposure of the *B.t.i.* particles to temperatures above 70° or 80° Celsius—depending upon the exposure time, which is inversely correlated with temperature—will cause the *B.t.i.* to suffer a protein denaturization, resulting in a change in its molecular structure and a loss of its activity. Thus, it would be impractical to attempt to incorporate *B.t.i.* into a thermoplastic or elastomeric strip of material, in view of the molding temperatures likely to be encountered. Moreover, even if the B.t.i. could be incorporated into a polymer or elastomeric matrix without substantially limiting or destroying its efficacy, these B.t.i. particles are agglomerations of relatively large molecules and are incapable of migrating within a polymer or elastomeric matrix. Hence, they would not even be released, since the active protein toxin has a molecular weight of approximately 28 megadaltons. The aforementioned methods are efficient, but are performed at high monetary costs to mosquito districts and taxpayers. Ultimately, the mosquitoes sought to be controlled are those noticed readily by humans, i.e. mosquitoes and blood-sucking flies that draw blood meals from humans.

Thus, numerous severe problems exist with the mosquito extermination methods that use chemical insecticides. As such, an alternative approach toward arthropod surveillance and control has been developed. One such promising method is the use of chemicals as attractants for mosquitoes and other arthropods that prey on human and animal hosts. The combination of highly effective chemical attractants with efficient traps allows for a control method to be developed similar to that used to control the Tsetse fly in Africa (Vale and Hall, *Bull. Ent. Res.*, 75, 219–231 (1985)). Because effective attractants are known for the Tsetse fly, a control method using only baited traps was developed and is very effective.

Current surveillance techniques rely on light traps or other traps which are relatively inefficient in mosquito collection. Sentinel chickens are used to assess transmission risk of encephalitis to humans in a local area. Better traps via more efficient and less expensive lures or baits would greatly aid in this endeavor. One example of a trap, U.S. Pat. No. 5,657,756 to Nicosia, 1997, involves collection and trapping of arthropods using warmed circulated fluid.

Carbon dioxide has been shown to attract mosquitoes. Willis, *J. Exp. Zool.*, 121, 149–179 (1952), discloses that *Aedes aegypti* (mosquitoes) are attracted to carbon dioxide. From amputation experiments on female *Aedes aegypti*, it was discovered that carbon dioxide receptors were located on the antennae. The role of carbon dioxide in the attraction of mosquitoes to hosts also has been the subject of numerous laboratory studies. Rudolfs, *N.J. Agric. Exp. Sta. Bull.*, 367 (1922), and Gouck, *J. Econ. Entomol.*, 55, 386–392 (1962), describe carbon dioxide as an activator, rather than an actual attractant.

Acree, *Science*, 1346–7 (1968), discloses that L-lactic acid, isolated from the human hand, attracts female *Aedes aegypti*. It also discloses that carbon dioxide is necessary to observe this attraction.

Wensler, *Can. J. Zool.*, 50, 415–420 (1972), discloses the use of ethyl ether soluble honey odors to attract *Ae. aegypti*.

Compositions consisting of lactic acid analogues and carbon dioxide have also been shown to attract mosquitoes. Carlson, *J. Econ. Entomol.*, 66, 329–331 (1973), discloses that some tested analogues of lactic acid had equivalent attraction to L-lactic acid, but this was not true at all tested doses. The highest reported attraction was 40% of female *Ae. aegypti*.

Bar-Zeev, *J. Med. Entomol.*, 14, 113–20 (1977), discloses that a composition consisting solely of lactic acid and carbon dioxide attracts *Ae. aegypti*. Here, the lactic acid was dissolved in acetone, similar to the use of methanol for the invention described in this application. It is clearly stated that the acetone solvent was evaporated from the filter paper prior to the carbon dioxide being allowed to pass into the flask. Acetone was chosen for its properties as a solvent, i.e., good ability to dissolve L-lactic acid and high volatility resulting in rapid evaporation or drying.

Price, *J. Chem. Ecol.*, 5, 383–95 (1979), discloses that human emanations and carbon dioxide attract female *An. quadrimaculatus*.

Lactic acid was shown to attract mosquitoes such as virgin *Ae. aegypti* (mosquitoes) by Davis, *J. Insect Physiol.*, 30, 211–15 (1984).

Gillies, *Bull. Entomol. Res.*, 70, 525–32 (1980), reviews the use of carbon dioxide to activate and attract mosquitoes.

Schreck, *J. Chem. Ecol.*, 8, 429–38 (1981), discloses that materials isolated from human hands, other than L-lactic acid, attract female *Ae. aegypti* and *An. quadrimaculatus* mosquitoes.

Lactic acid, in combination with phosphorous-containing compounds have been shown to attract mosquitoes. Ikeshoji, *Jpn. J. Sanit. Zool.*, 38, 333–38 (1987), discloses lactic acid and hempa; lactic acid and metepa; lactic acid, metepa and olive oil; and lactic acid and DDVP attract mosquitoes.

Lactic acid-related compounds have also been tested as mosquito attractants by electrophysiology. Davis, *J. Insect Physiol.*, 34, 443–49 (1988), discloses that neurons in the antennae are excited by L-lactic acid, and that analogues of lactic acid, e.g., carboxylic acids, alcohols, hydroxyacids, aldehydes, thiols and haloacids were tested for neuron response. It was shown that no compound elicited as high of a relative responsiveness toward lactic acid-excited cells as did lactic acid itself.

It has been shown that carbon dioxide, in combination with other chemicals, serves as an attractant for mosquitoes. Takken and Kline, *J. Am. Mosq. Control Assoc.*, 5, 311–6 (1989), disclose 1-octen-3-ol (octenol) and carbon dioxide as mosquito attractants. Van Essen, *Med. Vet. Entomol.*, 63–7 (1993), discloses the use of carbon dioxide, octenol, and light to attract several species of mosquitoes. Takken, *J. Insect Behavior*, 10, 395–407 (1997), discloses that a composition consisting solely of carbon dioxide, acetone and octenol attracts several species of mosquitoes.

Kline, *Med. Vet. Entomol.*, 4, 383–91 (1990), discloses that honey extract, octenol, carbon dioxide, L-lactic acid plus carbon dioxide, L-lactic acid plus octenol plus carbon dioxide attract mosquitoes well and butanone plus carbon dioxide, and phenol alone are less effective.

Schreck, *J. Am. Mosq. Control Assoc.*, 6, 406–10 (1990), discloses that materials isolated from human skin attract female *Ae. aegypti* and *An. quadrimaculatus* (mosquitoes), and the level of attraction, transferred to glass, varies from person to person. It also discloses that differences in attraction level are present depending on the body location origin of the material.

Takken, *Insect Sci. Applic.*, 12, 287–95 (1991), reviews mosquito attractants and lists acids, alone or in combination with other amino acids that are attractive for mosquitoes.

Eiras, *Bull. Entomol. Res.*, 81, 151–60 (1991), discloses that lactic acid, carbon dioxide, human sweat and thermal convection currents attract female *Ae. aegypti*.

Carlson, *J. Med. Entomol.*, 29, 165–70 (1992), discloses that the release of carbon dioxide from the human hand is negligible and therefore is not a factor in the attraction of *Ae. aegypti* (mosquitoes) to the human hand.

Bowen, *J. Insect Physiol.*, 40, 611–15 (1994), discloses that lactic acid sensitive receptors are present in *Ae. atropalpus*.

Eiras, *Bull. Entomol. Res.*, 84, 207–11 (1994), discloses that lactic acid in combination with carbon dioxide has been shown to attract mosquitoes.

Charlwood, *Ann. Trop. Med. Parasitol.*, 89, 327–9 (1995), discloses the mosquito-mediated attraction of female mosquitoes to hosts. Several species of mosquitoes were more attracted to a host, e.g., human leg, which already had mosquitoes feeding than a host which had no mosquitoes feeding on the host (termed "invitation effect"). An apparent pheromone, which was given off by the feeding mosquitoes, was speculated to attract other mosquitoes to the host.

DeJong and Knols, *Experientia*, 51, 80–4 (1995), discloses that different malaria mosquito species (*An. gambiae* s.s. and *An. atroparvus*) prefer different biting sites on the human body. DeJong and Knols, *Acta Tropica*, 59, 333–5 (1995), disclose that *An. gambiae* is attracted to carbon dioxide.

Bernier, Ph.D. Dissertation, University of Florida (1995), discloses the presence of lactic acid, glycerol, and long chain acids and alcohols on the skin, as well as other chemicals for a total of over 300 compounds. Some of these were identified and examined as candidate attractants.

Geier, in Olfaction in Mosquito-Host Interactions, 132–47 (1996), discloses that carbon dioxide alone is an attractant and that lactic acid alone is a mild attractant, but that the two act as a synergistic attractant. It also discloses that fractions of ethanol washings from human skin are attractive.

Knols and DeJong, *Parasitol. Today*, 12, 159–61 (1996), disclose that carbon dioxide in combination with Limburger cheese, serves as an attractant for female *An. gambiae*. It was suggested that mosquitoes are attracted to odors emanating from feet and ankles and this odor resembles Limburger cheese. It was also suggested that the odor of Limburger cheese was due to bacteria involved in cheese production which originate in human skin; cornyeform bacteria, in particular strains of *Brevibacterium linens*, which is closely related to *Br. epidermidis*, which forms part of the normal microflora of human feet, methanethiol, a pungent sulfur compound which is metabolized from L-methionine liberated during proteolytic activity and reported to contribute substantially to both cheese and foot odor; or the significant quantities of short-chained fatty acids in Limburger cheese.

McCall, *J. Med. Entomol.*, 33, 177–9 (1996), discloses that *Ae. aegypti* (mosquitoes) were attracted to volatile constituents of mouse odor, but did not identify potential chemicals.

Knols, *Bull. Entomol. Res.*, 87, 151–9 (1997), discloses the use of Limburger cheese (the acid and non-acid solvent extracted fractions) to attract *An. gambiae* (mosquitoes). Nineteen saturated and unsaturated aliphatic fatty acids, ranging in carbon chain lengths from $C_2$–$C_{18}$ were identified in Limburger cheese.

Mboera, *J. Vector Ecol.*, 23, 107–13 (1998), disclosed that *Culex quinquefasciatus* is attracted to a worn stocking and that carbon dioxide plus body odor did not increase response.

Kline, *J. Vector. Ecol.*, 23, 186–94 (1998), disclosed that in olfactometer tests, the human hand or worn sock attracted 80% and 66%, respecively, of *Ae. aegypti* in the cage. In comparison, Limburger cheese attracted 6.4%, and the control 0.0% in the olfactometer.

Bernier, *Anal. Chem.*, 71, 1–7 (1999), discloses the method for analysis of skin emanations, including the identification of lactic acid, glycerol, $C_{12}$–$C_{18}$ carboxylic acids and $C_4$–$C_{11}$ aldehydes.

Takken and Knots, *Annu. Rev. Entomol.*, 44, 131–57 (1999), reviewed odor-mediated behavior of afrotropical mosquitoes, reaffirming carbon dioxide as the best known mosquito kairomone.

Braks and Takken, *J. Chem. Ecol.*, 25 663–72 (1999), disclose that 2-day-old incubated sweat became attractive to *An. gambiae*.

Various chemicals have been disclosed as attractants for mosquitoes. U.S. Pat. No. 4,818,526 to Wilson discloses the use of dimethyl disulfide and dibutyl succinate and combinations thereof as attractants for Culicidae (mosquitoes).

U.S. Pat. No. 4,907,366 to Balfour (1990) discloses the use of a composition consisting solely of lactic acid, carbon dioxide, water, and heat to attract mosquitoes.

PCT WO 98/26661 to Justus discloses mixtures of L-lactic acid and its sodium salt, glycerol, and cheese extracts, with and without unsaturated long chain carboxylic acids, alcohols and an amide as attractive for *Ae. aegypti*. The glycerol, as well as other components described as equivalent to the glycerol, appear to make the composition substantive, so that it does not evaporate immediately in a rapid pulse. However, the active ingredients from Limburger cheese, which are the attractant chemicals, are not disclosed within the document, nor were statistical data reported for the results used in the examples.

Several of the above-mentioned chemicals and chemical compositions have been employed to attract any of the hundreds of species of mosquitoes and related arthropods that utilize humans and animals as their hosts. In fact, many of the disclosed compositions have been claimed to be active as attractants for mosquitoes. The activities of these attractants are often inconsistent and below 50% attraction response in laboratory experiments. More specifically, none of the disclosed compositions have been able to attract mosquitoes on a consistent basis as efficiently as, or more efficiently than the human body. As such, the human body has been examined repeatedly to provide clues regarding the chemical compositions disclosed. Thus, while chemicals and chemical compositions may have been active in attracting mosquitoes, none have been classified as successful for mosquito attraction as those reported in this document.

A long-felt need therefore exists for chemical compositions that can be employed safely in the environment, and that exhibit a synergistic effect for attracting mosquitoes wherein the compositions are more efficient than the human body in attracting mosquitoes. The present invention satisfies this need. Current mosquito traps often use carbon dioxide, which in the prior art was needed for efficient collection and surveillance. The present invention obviates the need for large carbon dioxide gas cylinders or dry ice by providing mosquito attractants that perform as well as, and more efficiently in place of, carbon dioxide. Although carbon dioxide is not necessary, it can still be included to release blends, as some insects may be attracted only with its inclusion.

SUMMARY OF THE INVENTION

The present invention provides compositions that efficiently attract arthropods (e.g., mosquitoes). Accordingly there is provided a composition comprising:

(A) an effective amount of at least one compound of formula I

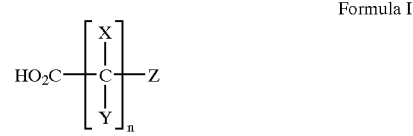

Formula I wherein each X is independently H, halogen, OH, SH, oxo, or ($C_1$–$C_8$)alkyl group;

each Y is independently H or ($C_1$–$C_8$)alkyl group,

Z is H, OH, SH, COOH, or ($C_1$–$C_8$)alkyl group;

n is an integer between 1 and 10, inclusive;

and salts thereof; and an effective amount of at least one compound from group II wherein group II compounds include a ketone having 3–10 carbon atoms, carbon dioxide, ($C_2$–$C_{10}$)alkene, ($C_1$–$C_{10}$)aldehyde, an alcohol having 1–8 carbon atoms, a halogenated compound containing 1–8 carbon atoms, a nitrile containing 2–4 carbon atoms, an ether containing 3–10 carbon atoms, ($C_6$–$C_{10}$)aryl group, a sulfide containing 1–8 carbon atoms and ($C_3$–$C_{10}$) heterocyclic group;

wherein any one or more of the ($C_6$–$C_{10}$)aryl group or ($C_3$–$C_{10}$)heterocyclic group may be substituted at any one or more positions with a substituent selected from the group consisting of H, oxo, halogen, OH, SH, COOH, COO($C_1$–$C_8$)alkyl group, ($C_1$–$C_8$)alkyl group, ($C_1$–$C_8$)alkyl sulfide and ($C_1$–$C_8$)alkyl group;

and salts thereof;

wherein the composition is effective to attract arthropods; or (B) a composition comprising an effective amount of tartaric acid or an acceptable salt thereof; and an effective amount of at least one compound from group II wherein group II compounds include a ketone having 3–10 carbon atoms, ($C_2$–$C_{10}$)alkene, ($C_1$–$C_{10}$) aldehyde, an alcohol having 1–8 carbon atoms, a halogenated compound containing 1–8 carbon atoms, a nitrile containing 2–4 carbon atoms, an ether containing 3–10 carbon atoms, carbon dioxide, ($C_6$–$C_{10}$)aryl group, a sulfide containing 1–8 carbon atoms and ($C_3$–$C_{10}$)heterocyclic group;

wherein any one or more of the ($C_6$–$C_{10}$)aryl or ($C_3$–$C_{10}$) heterocyclic may be substituted at any one or more positions with a substituent selected from the group consisting of H, oxo, halogen, OH, SH, COOH, COO ($C_1$–$C_8$)alkyl group, ($C_1$–$C_8$)alkyl group, ($C_1$–$C_8$)alkyl sulfide and ($C_1$–$C_8$)alkyl substituted with at least one substituent selected from the group consisting of H, OH, SH and halogen;

and salts thereof; wherein the composition is effective to attract arthropods; or (C) a composition comprising an effective amount of at least one

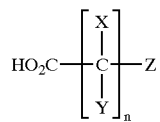

Formula I compound of formula I wherein each X is independently H, halogen, OH, SH, oxo, ($C_1$–$C_8$)alkyl, or ($C_1$–$C_8$)alkyl substituted with at least one substituent selected from the group consisting of H, OH, SH and halogen;

each Y is independently H, ($C_1$–$C_8$)alkyl, or ($C_1$–$C_8$)alkyl substituted with at least one substituent selected from the group consisting of H, OH, SH and halogen, or Y is absent when X is oxo;

Z is H, OH, SH, COOH, ($C_1$–$C_8$)alkyl, or ($C_1$–$C_8$)alkyl substituted with at least one substituent selected from the group consisting of H, OH, SH and halogen;

n is an integer between 1 and 10, inclusive;

and acceptable salts thereof;

and an effective amount of at least one compound from group II wherein group II compounds include a ketone having 3–10 carbon atoms, ($C_2$–$C_{10}$)alkene, ($C_1$–$C_{10}$) aldehyde, an alcohol having 1–8 carbon atoms, a halogenated compound containing 1–8 carbon atoms, a nitrile containing 2–4 carbon atoms, an ether containing 3–10 carbon atoms, carbon dioxide, ($C_6$–$C_{10}$)aryl group, a sulfide containing 1–8 carbon atoms and ($C_3$–$C_{10}$)heterocyclic group;

and salts thereof;

with the proviso that the compound of formula I does not consist solely of glycolic acid, oxalic acid, acetic acid, hydraacrylic acid, pyruvic acid, glyceric acid, 3-hydroxypyruvic acid, malonic acid, 3-hydroxybutyric acid, 2-methyllactic acid, 2-hydroxybutyric acid, 2-oxobutyric acid, isobutyric acid, butyric acid, malic acid, 2-oxovaleric acid, 2-hydroxyvaleric acid, 2-hydroxyvaleric acid, valeric acid, isovaleric acid, 2-methylvaleric acid, hexanoic acid, mercaptoacetic acid, thiolactic acid, 3-mercaptopropionic acid, thiopropionic acid, 3-mercaptopropionic acid, 2-bromopropionic acid, 2-bromobutyric acid, 2-chloropropionic acid, 3-chloropropionic acid, lactic acid or formic acid;

and salts thereof;

wherein the composition is effective to attract arthropods.

The present invention provides compositions that efficiently attract arthropods (e.g., mosquitoes). Accordingly there is provided a composition

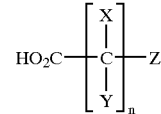

Formula I comprising an effective amount of at least one compound of formula I wherein each X is independently H, halogen, OH, SH, oxo, ($C_1$–$C_8$)alkyl group;

each Y is independently H, ($C_1$–$C_8$)alkyl group,

Z is H, OH, SH, COOH, or ($C_1$–$C_8$)alkyl group;

n is an integer between 1 and 10, inclusive;

and salts thereof; and an effective amount of at least one compound from group II wherein group II compounds include a ketone having 3–10 carbon atoms, carbon dioxide, ($C_2$–$C_{10}$)alkene, ($C_1$–$C_{10}$)aldehyde, an alcohol having 1–8 carbon atoms, a halogenated compound containing 1–8 carbon atoms, a nitrile containing 2–4 carbon atoms, an ether containing 3–10 carbon atoms, ($C_6$–$C_{10}$)aryl group, a sulfide containing 1–8 carbon atoms and ($C_3$–$C_{10}$) heterocyclic group;

wherein any one or more of the ($C_6$–$C_{10}$)aryl group or ($C_3$–$C_{10}$)heterocyclic group may be substituted at any one or more positions with a substituent selected from the group consisting of H, oxo, halogen, OH, SH, COOH, COO($C_1$–$C_8$)alkyl group, ($C_1$–$C_8$)alkyl group, ($C_1$–$C_8$)alkyl sulfide, O—($C_1$–$C_8$)alkyl; ($C_1$–$C_8$)alkyl group, and $NR_1R_2$ wherein $R_1$ and $R_2$ are each independently selected from the group consisting of ($C_1$–$C_8$)alkyl and H;

and salts thereof;

wherein the composition is effective to attract arthropods.

The present invention provides methods of attracting arthropods (e.g., mosquitoes) comprising the step of exposing the environment with a composition comprising an effective amount of a combination of:

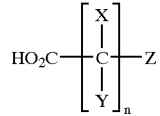

Formula I (A) an effective amount of at least one compound of formula I
wherein each X is independently H, halogen, OH, SH, oxo, $(C_1-C_8)$alkyl group;
each Y is independently H, $(C_1-C_8)$alkyl group,
Z is H, OH, SH, COOH, or $(C_1-C_8)$alkyl group;
n is an integer between 1 and 10, inclusive;
and salts thereof; and
an effective amount of at least one compound from group II wherein group II compounds include a ketone having 3–10 carbon atoms, carbon dioxide, $(C_2-C_{10})$alkene, $(C_1-C_{10})$aldehyde, an alcohol having 1–8 carbon atoms, a halogenated compound containing 1–8 carbon atoms, a nitrile containing 2–4 carbon atoms, an ether containing 3–10 carbon atoms, $(C_6-C_{10})$aryl group, a sulfide containing 1–8 carbon atoms and $(C_3-C_{10})$heterocyclic group;
wherein any one or more of the $(C_6-C_{10})$aryl group or $(C_3-C_{10})$heterocyclic group may be substituted at any one or more positions with a substituent selected from the group consisting of H, oxo, halogen, OH, SH, COOH, COO$(C_1-C_8)$alkyl group, $(C_1-C_8)$alkyl group, $(C_1-C_8)$alkyl sulfide, O—$(C_1-C_8)$alkyl; $(C_1-C_8)$alkyl group, and $NR_1R_2$ wherein $R_1$ and $R_2$ are each independently selected from the group consisting of $(C_1-C_8)$alkyl and H;
and salts thereof; or
(B) a composition comprising an effective amount of tartaric acid or an acceptable salt thereof; and
an effective amount of at least one compound from group II wherein group II compounds include a ketone having 3–10 carbon atoms, $(C_2-C_{10})$alkene, $(C_1-C_{10})$aldehyde, an alcohol having 1–8 carbon atoms, a halogenated compound containing 1–8 carbon atoms, a nitrile containing 2–4 carbon atoms, an ether containing 3–10 carbon atoms, carbon dioxide, $(C_6-C_{10})$aryl group, a sulfide containing 1–8 carbon atoms and $(C_3-C_{10})$heterocyclic group;
wherein any one or more of the $(C_6-C_{10})$aryl group or $(C_3-C_{10})$heterocyclic group may be substituted at any one or more positions with a substituent selected from the group consisting of H, oxo, halogen, OH, SH, COOH, COO$(C_1-C_8)$alkyl group, $(C_1-C_8)$alkyl group, $(C_1-C_8)$alkyl sulfide, O—$(C_1-C_8)$alkyl; $(C_1-C_8)$alkyl group, and $NR_1R_2$ wherein $R_1$ and $R_2$ are each independently selected from the group consisting of $(C_1-C_8)$alkyl and H;
and salts thereof;
wherein the composition is effective to attract arthropods; or
(C) a composition comprising an effective amount of at least one

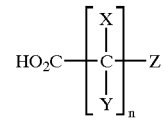

Formula I compound of formula I
wherein each X is independently H, halogen, OH, SH, oxo, $(C_1-C_8)$alkyl, or $(C_1-C_8)$alkyl substituted with at least one substituent selected from the group consisting of H, OH, SH and halogen;
each Y is independently H, $(C_1-C_8)$alkyl, or $(C_1-C_8)$alkyl substituted with at least one substituent selected from the group consisting of H, OH, SH and halogen, or Y is absent when X is oxo;
Z is H, OH, SH, COOH, $(C_1-C_8)$alkyl, or $(C_1-C_8)$alkyl substituted with at least one substituent selected from the group consisting of H, OH, SH and halogen;
n is an integer between 1 and 10, inclusive;
and acceptable salts thereof;
and an effective amount of at least one compound from group II wherein group II compounds include a ketone having 3–10 carbon atoms, $(C_2-C_{10})$alkene, $(C_1-C_{10})$aldehyde, an alcohol having 1–8 carbon atoms, a halogenated compound containing 1–8 carbon atoms, a nitrile containing 2–4 carbon atoms, an ether containing 3–10 carbon atoms, carbon dioxide, $(C_6-C_{10})$aryl group, a sulfide containing 1–8 carbon atoms and $(C_3-C_{10})$heterocyclic group;
and salts thereof;
with the proviso that the compound of formula I does not consist solely of glycolic acid, oxalic acid, acetic acid, hydraacrylic acid, pyruvic acid, glyceric acid, 3-hydroxypyruvic acid, malonic acid, 3-hydroxybutyric acid, 2-methyllactic acid, 2-hydroxybutyric acid, 2-oxobutyric acid, isobutyric acid, butyric acid, malic acid, 2-oxovaleric acid, 2-hydroxyvaleric acid, 2-hydroxyvaleric acid, valeric acid, isovaleric acid, 2-methylvaleric acid, hexanoic acid, mercaptoacetic acid, thiolactic acid, 3-mercaptopropionic acid, thiopropionic acid, 3-mercaptopropionic acid, 2-bromopropionic acid, 2-bromobutyric acid, 2-chloropropionic acid, 3-chloropropionic acid, lactic acid or formic acid;
and salts thereof.

The present invention provides methods of attracting arthropods (e.g., mosquitoes) comprising the step of exposing the environment with a composition comprising an effective amount of a compound of formula I

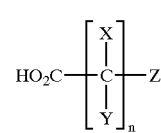

Formula I wherein each X is independently H, halogen, OH, SH, oxo, $(C_1-C_8)$alkyl group;
each Y is independently H, $(C_1-C_8)$alkyl group,
Z is H, OH, SH, COOH, or $(C_1-C_8)$alkyl group;
n is an integer between 1 and 10, inclusive;
and salts thereof; and an effective amount of at least one compound from group II wherein group II compounds include a ketone having 3–10 carbon atoms, carbon dioxide, $(C_2–C_{10})$alkene, $(C_1–C_{10})$aldehyde, an alcohol having 1–8 carbon atoms, a halogenated compound containing 1–8 carbon atoms, a nitrile containing 2–4 carbon atoms, an ether containing 3–10 carbon atoms, $(C_6–C_{10})$aryl group, a sulfide containing 1–8 carbon atoms and $(C_3–C_{10})$ heterocyclic group;

wherein any one or more of the $(C_6–C_{10})$aryl group or $(C_3–C_{10})$heterocyclic group may be substituted at any one or more positions with a substituent selected from the group consisting of H, oxo, halogen, OH, SH, COOH, COO$(C_1–C_8)$alkyl group, $(C_1–C_8)$alkyl group, $(C_1–C_8)$alkyl sulfide, O—$(C_1–C_8)$alkyl; $(C_1–C_8)$alkyl group, and $NR_1R_2$ wherein $R_1$ and $R_2$ are each independently selected from the group consisting of $(C_1–C_8)$alkyl and H;

and salts thereof;

wherein the composition is effective to attract arthropods.

The present invention entails blends of compounds that have not been previously combined, in either volume or composition for attracting mosquitoes. The novel combination of compounds of the present invention serve as effective arthropod attractants. The novel compositions of the present invention may be more effective than humans as arthropod attractants.

It has surprisingly been discovered that the compositions of the present invention are effective in attracting arthropods, e.g., mosquitoes. In addition, it has surprisingly been discovered that compositions of the compounds of formula I and the compounds of group II exhibit a synergistic effect in attracting arthropods, e.g., mosquitoes. This synergistic effect, in many cases, enables the compositions of the present invention to attract arthropods as well as, or better than humans. In addition, the compositions of the present invention obviate the need, in many cases, for the use of carbon dioxide in arthropod traps.

DETAILED DESCRIPTION OF THE INVENTION

The following definitions are used, unless otherwise described: halo is fluoro, chloro, bromo, or iodo.

Alkyl, denotes both straight, cyclic and branched groups; but reference to an individual radical such as "propyl" embraces only the straight chain radical, a branched chain isomer such as "isopropyl" being specifically referred to.

Aryl denotes a phenyl radical or an ortho-fused bicyclic carbocyclic radical having about nine to ten ring atoms in which at least one ring is aromatic.

Heterocyclic encompasses a radical attached via a ring carbon of a monocyclic ring containing five or six ring atoms consisting of carbon and one to four heteroatoms each selected from the group consisting of non-peroxide oxygen, sulfur, and N(X) wherein each X is absent (e.g., —N=) or is H, O, $(C_1–C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

As is well understood in the art, substitution of compounds and groups may be highly desirable for effecting either physical (e.g., volatility, melting point, softening point, viscosity, molecular weight and size, solubility, hydrophilicity, oleophilicity, and the like) or chemical properties. Where a substituent is referred to as a "group," that term implies that the compound may be substituted or not within the practice of the present invention. Where the substituent is referred to as a moiety or without any qualification, no substitution is contemplated. For example, alkyl group is inclusive of methyl, ethyl, propyl, butyl, isopropyl, octyl, dodecyl, cyclohexyl, 1-chlorobutyl, 2-hydroxypentyl, 4-cyanobutyl, and the like. On the other hand, and alkyl moiety or an alkyl would include only such substituents as methyl, ethyl, propyl, butyl, isopropyl, octyl, dodecyl, and cyclohexyl. Similarly, reference to a material as a compound having a central nucleus of a stated formula would include any compound, with any substituent, which did not alter the bond structure of the shown formula.

It will be appreciated by those skilled in the art that compositions of the present invention will comprise one or more compounds that have one or more chiral centers. Such compounds may exist and be isolated as optically active and racemic forms. Some compounds may exhibit polymorphism. It is to be understood that the present invention encompasses any racemic, optically-active, polymorphic, or stereoisomeric form, or mixtures thereof, of a compound of the invention, that possesses the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) or using other tests which are well known in the art.

Specific and preferred values listed below for radicals, genera, chemicals, substituents, and ranges, are for illustration only and they do not exclude other defined values or other values within defined ranges for the radicals, genera, chemicals and substituents.

It is appreciated that "arthropod" is a member of the phylum Arthropoda, which is the largest phylum in the animal kingdom, comprising about 75% of all animals that have been described. The estimated number of arthropod species is between 1,000,000 and 2,000,000. Arthropods vary in size from the microscopic mites to the giant decapod crustaceans.

The phylum Arthropoda includes many families of insects that are of a medical and veterinary importance, e.g., mosquitoes (Culicidae), blackflies (Simuliidae), sand flies (Phlebotominae), biting midges (Ceratopogonidae), horseflies (Tabanidae), tsetse flies (Glossinidae), stable flies and house flies (Muscidae), fleas (Siphonaptera), lice (Anoplura), triatomine bugs (Triatominae), soft ticks (Argasidae) and hard ticks (Ixodidae).

A specific Arthropoda is mosquitoes (Culicidae), blackflies (Simuliidae), sand flies (Phlebotominae), biting midges (Ceratopogonidae), horseflies (Tabanidae), tsetse flies (Glossinidae), stable flies and house flies (Muscidae), fleas (Siphonaptera), lice (Anoplura), triatomine bugs (Triatominae), soft ticks (Argasidae) and hard ticks (Ixodidae).

It is appreciated that "mosquito" can be any of the mosquitoes belonging to the suborder diptera known as Nematocera. This suborder includes the family Culicidae. The 3400 or so species of mosquitoes are arranged in 38 genera. The Culicidae are divided into three subfamilies: the Anophelinae, including the well-known genus Anopheles, many species of which are responsible for the transmission of malaria; the Toxorhynchitinae, the large larvae of which eat other mosquito larva; and the Culicinae which, with about 2930 species in about 34 genera, are divided into two tribes: the Culicini and the Sabethini. The Culcine mosquitoes include such well known genera as Culex, Aedes and Mansonia. The sebethene mosquitoes include Sabethes, Wyeomyia and Malaya.

A specific mosquitoe is the genera Culex, Aedes, Psorophora, Wyeomyia, Mansonia, Coquilletidia or Anopheles.

A specific arthropod is a mosquito belonging to the genera Culex, Aedes, Mansonia, Wyeomyia, Psorophora, Coquilletidia or Anopholes.

Another specific arthropod is Simulidae, Triatoninae, Siphonaptera, Tabanidae, Culicoides, Phleobotomines, Muscidae, Glossinidae, Ixodidae or Argasidae.

Specifically, $(C_1-C_8)$alkyl can include, for example, methyl, ethyl, propyl, isopropyl, butyl, iso-butyl, sec-butyl, pentyl, sec-pentyl, iso-pentyl, hexyl, sec-hexyl, iso-hexyl, heptyl, sec-heptyl, iso-hectyl and octyl.

A specific $(C_1-C_8)$alkyl is methyl, ethyl, propyl, isopropyl, butyl, iso-butyl, sec-butyl, pentyl, sec-pentyl or hexyl. Another specific $(C_1-C_8)$alkyl is methyl. Another specific $(C_1-C_8)$alkyl is ethyl. Another specific $(C_1-C_8)$alkyl is propyl.

Specifically $(C_6-C_{10})$aryl, for example, can be a central nucleus comprising phenyl, indenyl or naphthyl.

A specific $(C_6-C_{10})$aryl is phenyl.

$(C_6-C_{10})$aryl may optionally be substituted at any one or more positions with a substituent selected from the group consisting of H; oxo; halogen; OH; SH; COOH; COO$(C_1-C_8)$alkyl; $(C_1-C_8)$alkyl; $(C_1-C_8)$alkyl sulfide; $NR_1R_2$ wherein $R_1$ and $R_2$ are independently selected from H and $(C_1-C_6)$alkyl; and $(C_1-C_8)$alkyl substituted with at least one substituent selected from the group consisting of H, OH, SH and halogen.

In one specific embodiment, $(C_6-C_{10})$aryl is substituted with $CH_3$ and OH. In another specific embodiment, $(C_6-C_{10})$aryl is substituted with $CH_3$. In another embodiment, $(C_6-C_{10})$aryl is substituted with OH. In another embodiment, $(C_6-C_{10})$aryl is substituted with $NH_2$.

Another specific $(C_6-C_{10})$aryl is p-cresol, benzonitrile, phenol or toluene. Another specific $(C_6-C_{10})$aryl is p-cresol. Another specific $(C_6-C_{10})$aryl is benzonitrile. Another specific $(C_6-C_{10})$aryl is phenol. Another specific $(C_6-C_{10})$aryl is toluene.

$(C_3-C_{10})$heterocycle may be substituted at any one or more positions with a substituent selected from the group consisting of H, oxo, halogen, OH, SH, COOH, COO$(C_1-C_8)$alkyl, $(C_1-C_8)$alkyl, $(C_1-C_8)$alkyl sulfide and $(C_1-C_8)$alkyl substituted with at least one substituent selected from the group consisting of H, OH, SH and halogen.

In one embodiment, $(C_3-C_{10})$heterocycle is substituted with $CH_3$.

A specific $(C_3-C_{10})$heterocycle is furan, azole, dioxane, thiophene, thiazole or triazole.

A specific $(C_3-C_{10})$heterocycle is furan.

Specifically, X is H, halogen, OH, SH, oxo, $(C_1-C_8)$alkyl, or $(C_1-C_8)$alkyl substituted with at least one substituent selected from the group consisting of H, OH, SH and halogen.

A specific X is H. Another specific X is halogen. Another specific X is OH. Another specific X is SH. Another specific X is oxo. Another specific X is $(C_1-C_8)$alkyl. Another specific X is $(C_1-C_8)$alkyl substituted with at least one substituent selected from the group consisting of H, OH, SH and halogen. Another specific X is $CH_3$.

Specifically, Y is H, $(C_1-C_8)$alkyl, or $(C_1-C_8)$alkyl substituted with at least one substituent selected from the group consisting of H, OH, SH and halogen, or Y is absent when X is oxo.

A specific Y is H. Another specific Y is $(C_1-C_8)$alkyl. Another specific Y is $(C_1-C_8)$alkyl substituted with at least one substituent selected from the group consisting of H, OH, SH and halogen. Another specific Y is Y being absent.

Specifically, Z is H, OH, SH, COOH, $(C_1-C_8)$alkyl, or $(C_1-C_8)$alkyl substituted with at least one substituent selected from the group consisting of H, OH, SH and halogen.

A specific Z is H. Another specific Z is OH. Another specific Z is SH. Another specific Z is COOH. Another specific Z is $(C_1-C_8)$alkyl. Another specific Z is $(C_1-C_8)$alkyl substituted with at least one substituent selected from the group consisting of H, OH, SH and halogen.

Specifically, n is an integer between 1 and 10, inclusive.

A specific value for n is 1. Another specific value for n is 2. Another specific value for n is 3. Another specific value for n is 4. Another specific value for n is 5. Another specific value for n is 6. Another specific value for n is 7. Another specific value for n is 8. Another specific value for n is 9. Another specific value for n is 10.

The volatile component of skin extracts or hair extracts is the washings of skin or the washings of the shavings of hair, each blended with acetone or another suitable solvent. Although such washings of human skin or hair are not novel, the use of hair, saved hair or skin from an appropriate device not employing a shave cream can be mixed, or suspended in a suitable solvent as means to extract and release compounds attractive to arthropods. Many of the compounds found on hair are present due to skin oils, and in fact, shavings consist of both hair and dead skin cells. The same volatiles identified in Bernier, Ph.D. dissertation, University of Florida, 1995; and Bernier, et al., Analytical Chemistry, Vol. 71, No. 1, Jan. 1, 1999 are present on the hair and dead skin cells.

Compounds of formula I will contain at least one carboxylic acid group. Particular carboxylic acids for use in the present invention include lactic acid, glycolic acid, thiolactic acid and tartaric acid.

A specific compound of formula I is lactic acid. Another specific compound of formula I is glycolic acid. Another specific compound of formula I is thiolactic acid. Another specific compound of formula I is tartaric acid.

The chain lengths on the alkyl groups in formula I, particularly those inclusive of the alcohols and ketones, are important because of the need for effective levels of volatility for the individual and mixed compounds of the compositions of the invention. If significantly higher molecular weight ketones (e.g., greater than or equal to ten carbon atoms) or significantly higher molecular weight alcohols were used, the compounds and their mixtures would have reduced volatility and would not be effective, particularly over a wide area, as the compounds would not volatilize in sufficient amounts to be effective attractants over a significantly wide area. Thus, it is not likely that the higher molecular weight compounds will exhibit a synergistic effect because only one compound will be relatively volatile.

A specific compound of formula I is tartaric acid or an acceptable salt thereof. In such embodiment, the present invention is a composition comprising a combination of tartaric acid or an acceptable salt thereof; and at least one compound from group II wherein group II compounds include a ketone having 3–10 carbon atoms, $(C_2-C_{10})$ alkene, $(C_1-C_{10})$aldehyde, carbon dioxide, an alcohol having 1–8 carbon atoms, a halogenated compound containing 1–8 carbon atoms, a nitrile containing 2–4 carbon atoms, an ether containing 3–10 carbon atoms, carbon dioxide, $(C_6-C_{10})$aryl, a sulfide containing 1–8 carbon atoms and $(C_3-C_{10})$heterocyclic;

wherein any one or more of the $(C_6-C_{10})$aryl or $(C_3-C_{10})$ heterocyclic may be substituted at any one or more positions with a substituent selected from the group consisting of H; oxo; halogen; OH; SH; COOH; COO$(C_1-C_8)$alkyl; $(C_1-C_8)$ alkyl; $(C_1-C_8)$alkyl sulfide; $(C_1-C_8)$alkyl substituted with at least one substituent selected from the group consisting of H, OH, SH and halogen; and $NR_1R_2$ wherein $R_1$ and $R_2$ are independently selected from the group consisting of H and $(C_1-C_8)$alkyl;

and salts thereof (as defined for Group I, above).

In another embodiment, the present invention is a composition comprising an effective amount of a combination of at least one compound of

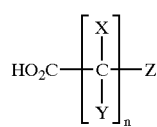

Formula I formula I wherein each X is independently H, halogen, OH, SH, oxo, $(C_1-C_8)$alkyl, or $(C_1-C_8)$alkyl substituted with at least one substituent selected from the group consisting of H, OH, SH and halogen;

each Y is independently H, $(C_1-C_8)$alkyl, or $(C_1-C_8)$alkyl substituted with at least one substituent selected from the group consisting of H, OH, SH and halogen, or Y is absent when X is oxo;

Z is H, OH, SH, COOH, $(C_1-C_8)$alkyl, or $(C_1-C_8)$alkyl substituted with at least one substituent selected from the group consisting of H, OH, SH and halogen;

n is an integer between 1 and 10, inclusive;

and salts thereof (as defined for Group I, above);

and an effective amount of at least one compound from group II wherein group II compounds include a ketone having 3–10 carbon atoms, $(C_2-C_{10})$alkene, $(C_1-C_{10})$ aldehyde, an alcohol having 1–8 carbon atoms, a halogenated compound containing 1–8 carbon atoms, a nitrile containing 2–4 carbon atoms, an ether containing 3–10 carbon atoms, carbon dioxide, $(C_6-C_{10})$aryl, a sulfide containing 1–8 carbon atoms and $(C_3-C_{10})$ heterocyclic;

wherein any one or more of the $(C_6-C_{10})$aryl or $(C_3-C_{10})$ heterocyclic may be substituted at any one or more positions with a substituent selected from the group consisting of H, oxo, halogen, OH, SH, COOH, COO $(C_1-C_8)$alkyl, $(C_1-C_8)$alkyl, $(C_1-C_8)$alkyl sulfide and $(C_1-C_8)$alkyl substituted with at least one substituent selected from the group consisting of H, OH, SH and halogen;

and salts thereof (as defined for Group I, above);

with the proviso that the compound of formula I does not consist solely of glycolic acid, oxalic acid, acetic acid, hydraacrylic acid, pyruvic acid, glyceric acid, 3-hydroxypyruvic acid, malonic acid, 3-hydroxybutyric acid, 2-methyllactic acid, 2-hydroxybutyric acid, 2-oxobutyric acid, isobutyric acid, butyric acid, malic acid, 2-oxovaleric acid, 2-hydroxyvaleric acid, 2-hydroxyvaleric acid, valeric acid, isovaleric acid, 2-methylvaleric acid, hexanoic acid, mercaptoacetic acid, thiolactic acid, 3-mercaptopropionic acid, thiopropionic acid, 3-mercaptopropionic acid, 2-bromopropionic acid, 2-bromobutyric acid, 2-chloropropionic acid, 3-chloropropionic acid, lactic acid or formic acid;

and salts thereof (as defined for Group I, above);

wherein the composition is effective to attract mosquitoes.

In the above embodiment, the compound of formula I includes one or more (e.g., 1, 2, or 3) compounds selecetd from the group consisting of glycolic acid; oxalic acid; acetic acid; hydraacrylic acid; pyruvic acid; glyceric acid; 3-hydroxypyruvic acid; malonic acid; 3-hydroxybutyric acid; 2-methyllactic acid; 2-hydroxybutyric acid; 2-oxobutyric acid; isobutyric acid; butyric acid; malic acid; 2-oxovaleric acid; 2-hydroxyvaleric acid; 2-hydroxyvaleric acid; valeric acid; isovaleric acid; 2-methylvaleric acid; hexanoic acid; mercaptoacetic acid; thiolactic acid; 3-mercaptopropionic acid; thiopropionic acid; 3-mercaptopropionic acid; 2-bromopropionic acid; 2-bromobutyric acid; 2chloropropionic acid; 3-chloropropionic acid; lactic acid and formic acid, in addition to one or more (e.g., 1, 2, or 3) compounds of formula I. It is appreciated that the compound of formula I may comprise two or more distinct compounds. In addition, one (or more) of the two or more distinct compounds of formula I may be one of the above-identified compounds. Moreover, any combination of the above-identified compounds is acceptable.

In another embodiment, the present invention provides a composition comprising an effective amount of a combination of at least one compound of formula I

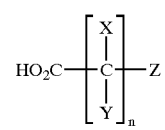

Formula I wherein each X is independently H, halogen, OH, SH, oxo, $(C_1-C_8)$alkyl, or $(C_1-C_8)$alkyl substituted with at least one substituent selected from the group consisting of H, OH, SH and halogen;

each Y is independently H, $(C_1-C_8)$alkyl, or $(C_1-C_8)$alkyl substituted with at least one substituent selected from the group consisting of H, OH, SH and halogen, or Y is absent when X is oxo;

Z is H, OH, SH, COOH, $(C_1-C_8)$alkyl, or $(C_1-C_8)$alkyl substituted with at least one substituent selected from the group consisting of H, OH, SH and halogen;

n is an integer between 1 and 10, inclusive;

and salts thereof (as defined for Group I, above);

and an effective amount of at least one compound from group II wherein group II compounds include a ketone having 3–10 carbon atoms, carbon dioxide, $(C_2-C_{10})$ alkene, $(C_1-C_{10})$aldehyde, an alcohol having 1–8 carbon atoms, a halogenated compound containing 1–8 carbon atoms, a nitrile containing 2–4 carbon atoms, an ether containing 3–10 carbon atoms, $(C_6-C_{10})$aryl, a sulfide containing 1–8 carbon atoms and $(C_3-C_{10})$ heterocyclic;

wherein any one or more of the $(C_6-C_{10})$aryl or $(C_3-C_{10})$ heterocyclic may be substituted at any one or more positions with a substituent selected from the group consisting of H, oxo, halogen, OH, SH, COOH, COO ($C_1$–$C_8$)alkyl, ($C_1$–$C_8$)alkyl, ($C_1$–$C_8$)alkyl sulfide and ($C_1$–$C_8$)alkyl substituted with at least one substituent selected from the group consisting of H, OH, SH and halogen;

and salts thereof (as defined for Group I, above);

wherein the composition is effective to attract mosquitoes.

Specifically, "ketone" is any compound containing one or more —C(C=O)C— groups. Particular ketones for use in the present invention will have between 3–10 carbon atoms, inclusive. More specifically, ketone can be acetone, butanone, 2-pentanone, 2-hexanone, 2-heptanone, 3-pentanone, 3-hexanone, 3-heptanone, 4-heptanone, 5-nonanone, 3-methyl-2-butanone, 4-methyl-2-pentanone, 3-penten-2-one, 3-buten-2-one, 3-hydroxy-2-butanone, 2,3-butanedione or 2,4-pentanedione.

A specific ketone is acetone. Another specific ketone is butanone. Another specific ketone is 2-pentanone. Another specific ketone is 2-hexanone. Another specific ketone is 2-heptanone. Another specific ketone is 3-pentanone. Another specific ketone is 3-hexanone. Another specific ketone is 3-heptanone. Another specific ketone is 4-heptanone. Another specific ketone is 5-nonanone. Another specific ketone is 3-methyl-2-butanone. Another specific ketone is 4-methyl-2-pentanone. Another specific ketone is 3-penten-2-one. Another specific ketone is 3-buten-2-one. Another specific ketone is 3-hydroxy-2-butanone. Another specific ketone is 2,3-butanedione. Another specific ketone is 2,4-pentanedione.

Specifically, "alkene" is any compound containing at least one C=C group. Particular alkenes for use in the present invention contain between 2 and 10 carbon atoms, inclusive. Particular alkenes for use in the present invention include aliphatic or cyclic alkenes. In addition, particular alkenes for use in the present invention include linear or branched alkenes. Particular alkenes for use in the present invention include isoprene, 1-heptene, 1-octene and 1-nonene.

A specific alkene is isoprene. Another specific alkene is 1-heptene. Another specific alkene is 1-octene. Another specific alkene is 1-nonene.

Specifically, "alcohol" is any compound containing at least one C(OH) group. Particular alcohols for use in the present invention will have between 1 and 8 carbon atoms, inclusive. Particular alcohols for use in the present invention may be aliphatic or cyclic alcohols. Particular alcohols for use in the present invention may be branched or straight chained alcohols. Particular alcohols for use in the present invention include methanol, ethanol, 1-hepten-3-ol and 1-octen-3-ol.

A specific alcohol is methanol. Another specific alcohol is ethanol. Another specific alcohol is 1-hepten-3-ol. Another specific alcohol is 1-octen-3-ol.

Specifically, ($C_1$–$C_{10}$)aldehyde is a compound containing at least one C(=O)H group and between 1 and 10 carbon atoms, inclusive. Particular aldehydes for use in the present invention include formaldehyde, acetaldehyde, butyraldehyde, isobutyraldehyde, nonanal and benzaldehyde.

A specific aldehyde is formaldehyde. Another specific aldehyde is acetaldehyde. Another specific aldehyde is butyraldehyde. Another specific aldehyde is isobutyraldehyde. Another specific aldehyde is nonanal. Another specific aldehyde is benzaldehyde.

Specifically, "halogenated compound" is any compound containing at least one C-X group wherein X is a halogen atom. The halogen may be fluorine, chlorine, bromine or iodine. It should be noted that one or more halogen atoms may be present in the halogenated compound. Particular halogenated compounds for use in the present invention include halogenated ($C_1$–$C_8$)alkyl such as methylene chloride, chloroform, carbon tetrachloride and bromoform.

A specific halogenated compound is methylene chloride. Another specific halogenated compound is chloroform. Another specific halogenated compound is carbon tetrachloride. Another specific halogenated compound is bromoform.

Specifically, "nitrile" is any compound containing at least one CN group. Particular nitriles for use in the present invention include acetonitrile, benzonitrile and phenylacetionitrile.

A specific nitrile is acetonitrile. Another specific nitrile is benzonitrile. Another specific nitrile is phenylacetonitrile.

Specifically, "ether" is any compound containing a C—O—C group. Particular ethers for use in the present invention will have between 3 and 10 carbon atoms, inclusive, particularly aliphatic compounds.

A specific ether is diethyl ether.

Specifically, "carbon dioxide" is represented by the formula $CO_2$. The carbon dioxide used in the present invention may exist as a gas or a solid. Carbon dioxide will normally exist as a gas at standard temperature and pressure. However, the carbon dioxide may be solid carbon dioxide, i.e., dry ice, in which case the carbon dioxide will sublime and eventually enter into the atmosphere as a gas. Alternatively, carbon dioxide may be delivered directly or indirectly from a cylinder or similar dispensing device. In such a case, the flow of carbon dioxide used may be monitored. As such, dry ice may be added to the other chemicals or carbon dioxide may be bubbled into the other chemicals from a carbon dioxide source. It should be noted that both forms of carbon dioxide are equally effective. However, cost and convenience may necessitate that one form be used to the exclusion of the other.

Specifically, "sulfide" is any compound containing at least one C-S group. Particular sulfides for use in the present invention will contain between 1 and 10 carbon atoms, inclusive and between 1 and 3 sulfur atoms, inclusive. Particular aliphatic sulfides for use in the present invention include carbon disulfide, dimethyl sulfide, diethyl sulfide, dimethyl disulfide, diethyl disulfide, methyl propyl disulfide, ethyl vinyl sulfide, dimethyl sulfoxide and dimethyl trisulfide.

A specific sulfide is carbon disulfide. Another specific sulfide is dimethyl sulfide. Another specific sulfide is diethyl sulfide. Another specific sulfide is dimethyl disulfide. Another specific sulfide is diethyl disulfide. Another specific sulfide is methyl propyl disulfide. Another specific sulfide is dimethyl trisulfide. Another specific sulfide is ethyl vinyl sulfide. Another specific sulfide is dimethyl sulfoxide.

Specifically, "oxo" is C(=O).

In one embodiment, a composition of the present invention comprises a compound of formula I and comprises a compound of group II.

In one embodiment of the present invention, a composition comprises a compound of formula I, wherein a compound of formula I is lactic acid and the composition comprises at least three compounds of group II, which are acetone, carbon dioxide and dimethyl sulfide.

Those of skill in the art will recognize that suitable compositions are formed by combining the compound or compounds of formula I with the compound or compounds of group II. The order of addition should not effect the activity of the resulting composition. However, cost and convenience may necessitate certain compounds be added in a certain order. It was found that convenience and cost dictated that any gases employed be added to other gases or liquids. Additionally, any solids employed should be added to liquids. The resulting mixtures were used without further preparation, although mixing is optional for each mixture developed.

In cases where compounds are sufficiently basic or acidic to form stable nontoxic acid or base salts, use of the compounds as salts may be appropriate. Examples of acceptable salts are organic acid addition salts formed with acids which form an acceptable anion, for example, tosylate, methanesulfonate, acetate, citrate, malonate, tartarate, succinate, benzoate, ascorbate, α-ketoglutarate, and α-glycerophosphate. Particular inorganic salts of the present invention may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

Specifically, "environment" is the surrounding land, air or water (or any combination thereof). The environment (i.e., surrounding area) may contain arthropods (e.g., mosquitoes, biting midges, etc) such that an effective amount of the composition will attract a significant portion of the arthropods from the environment.

Alternatively, the environment will not contain a significant amount of arthropods such that an effective amount of the composition will ensure that the composition will attract a significant portion of the arthropods subsequently existing in the environment, from the environment. In such an embodiment, the compositions of the present invention will prophylactically remove arthropods from the environment.

The compositions of the present invention may be added, in any form, to a commercial or home-made trap to enhance the collection of the arthropod. The composition may diffuse out or away from the trap with or without a gas stream (e.g., air, carbon dioxide, etc.) as a carrier.

As used herein, a trap is a device that ensnares an arthropod. Effective traps include those disclosed in Example 10, Table 10. Suitable traps are commercially available from American Biophysics, East Greenwich, R.I.; Bio Quip Products, Gardena, Calif.; John W. Hock Company, Gainesville, Fla.; and Bio Sensory, Inc., Windham Mills Technology Center, Wilimatic, Conn.

The compositions of the present invention may be delivered in vials or other sample containers. The compositions may exist as the chemical or chemicals of formula I in one vial or container, and the chemical or chemicals of the compound of group II in another separate vial or container. Alternatively, the composition may be blended together wherein the chemical or chemicals of formula I and the chemical or chemicals of the compound of group II may be blended together in one vial. The compositions, whether present in one or two vials, may optionally include a means of a controlled release.

The compositions of the present invention may be delivered in the gas phase, such as by a compressed cylinder. In addition, the composition existing in the gas phase, may optionally be mixed or unmixed with an inert carrier gas.

The efficacy of the compositions of the present invention in attracting arthropods, may be further enhanced by adding one or more of the chemical compositions of skin washings or hair washings as disclosed in Bernier, Ph.D. dissertation, University of Florida, 1995 or Bernier, et al., Analytical Chemistry, Vol. 71, No. 1, Jan. 1, 1999.

The efficacy of the compositions of the present invention in attracting arthropods, may be further enhanced by adding one or more of light, heat and moisture.

It is appreciated that those skilled in the art recognize that the compositions of the present invention include one or compounds of the formula I and one or more compounds of group II compounds. The compound or compounds of formula I may comprise about 1% to about 99%, by weight, of the total composition. In addition, the compound or compounds of the group II compounds may comprise about 1% to about 99% of the total composition, by weight.

Effective amounts or ratios of each compound forming the resulting composition as well as effective amounts of the resulting composition will depend upon the individual compound or compounds of formula I and the individual compound or compounds of group II. The amount of composition required for use will vary not only with the particular compounds selected but also with factors such as type of arthropod, weather conditions, the geographical area to be covered and the desired length of time in which the insects are to be attracted.

All chemicals used were purchased commercially from, e.g., Aldrich & Fluka Chemical, Milwaukee, Wis., and Lancaster Synthesis, Windham, N.H.

All publications and patents are incorporated by reference herein, as though individually incorporated by reference, as long as they are not inconsistent with the present disclosure. The invention is not limited to the exact details shown and described, for it should be understood that many variations and modifications may be made while remaining within the spirit and scope of the invention defined by the claims.

The invention will now be illustrated by the following non-limiting Examples, wherein unless otherwise specified, the tests were conducted with approximately 75 6–8 day old nulliparous female *Aedes aegypti*. The tests were conducted in an olfactometer (55 ft$^3$/min airflow, 80° F., 60% R.H.) as described by Posey, *J. Med. Entomol.*, 35, 330–334 (1998); and LA is lactic acid. Mosquitoes were allowed to settle at least one hour prior to testing. The olfactometer was cleaned after each battery of tests. Each battery consisted of three tests, conducted at 08:30, 11:00 and 13:00 hours local time. Each of the three tests was conducted in a separate cage. The control consisted of identical sample delivery devices and conditions compared to that of the treatment side. Both the treatment and control ports were opened and closed simultaneously when inserting a new treatment/control.

EXAMPLES

Example 1

Table 1 illustrates the effectiveness (in percentage caught of 75 female mosquitos) of lactic acid alone and of acetone alone as attractants for *Aedes aegypti*. It was shown that 200 µL lactic acid alone attracted an average of 26% of the mosquitoes. It was also shown that 500 µL acetone alone, evaporated from a 60 mm diameter glass petri dish, attracted an average of 51% of the mosquitoes.

TABLE 1

Compounds Screened in the Olfactometer

L-lactic acid response (%) with 200 μL of a 1 μg/1 μL methanolic solution, dried 3 minutes in a petri dish:

| | | | | | | | | | | | | |
|---|---|---|---|---|---|---|---|---|---|---|---|---|
| 25 | 31 | 57 | 12 | 23 | 29 | 5 | 27 | 7 | 7 | 7 | 14 | 36 |
| 26 | 28 | 52 | 31 | 44 | 60 | 4 | 20 | 22 | 25 | 29 | 15 | 24 |
| 26 | 25 | 19 | 8 | 16 | 27 | 48 | 64 | 23 | 14 | 22 | 25 | 25 |
| 20 | 13 | 14 | 21 | 23 | 52 | 40 | 17 | 31 | 36 | 25 | 9 | |

LA Avg: 1303/51 = 26%, n = 51 trials
Actone response (%) at 500 μL, plated on a small petri dish:
51 48 53 51
Acetone Avg: 203/4 = 51%, n = 4 trials

Example 2

Table 2 illustrates the effectiveness of several classes of compounds (e.g., ketones, carboxylic acids, alcohols, halogenated compounds, aldehydes, alkenes, nitriles, heterocyclic, sulfides, ethers, etc.) as attractants for *Aedes aegypti* mosquitoes. In addition, Table 2 also illustrates the synergistic effectiveness of these compounds with lactic acid as attractants for mosquitoes.

TABLE 2

Results of screening for compounds (high dose of 500 μL) with a mode of action similar to acetone are below. These compounds are also called "activators" or "activator 2" compounds where the number designation of activator denotes that those chemicals elicit different behaviors (e.g., probing, flight pattern) in attraction. Italicized numbers represent values or, when present, average values that capture greater than 50% of mosquitoes. (CK = check or control port):

| Compound/CLASS | Response (%) | Response with L-LA (%) | Δ[(Resp with LA)-Resp] (%) |
|---|---|---|---|
| carbon dioxide 5 ml/min | | *68* | |
| KETONES: | | | |
| acetone | 51 48 53 51 (*51%*) | 87 87 86 95 85 90 92 75 86 84 88 70 82 96 88 96 88 81. 95 97 97 93 95 90 82 80 95 (*88%*) | 37 |
| 2-butanone | 28 | *81* | 53 |
| 2-pentanone | 8 | *76* | 64 |
| 2-hexanone | 3 | *51* | 48 |
| 2-heptanone | 17 | 42 | 25 |
| 2-octanone | 8 | 16 | 8 |
| 2-nonanone | 8 | 12 | 4 |
| 2-decanone | 14 | 24 | 10 |
| 3-pentanone | 12 | 28 | 16 |
| 3-hexanone | 1 | 39 | 38 |
| 3-heptanone | 12 | 36 | 24 |
| 3-nonanone | 4 | 9 | 5 |
| 4-heptanone | 12 | 32 | 20 |
| 5-nonanone | 14 | 47 | 33 |
| 1-penten-3-one | 19 | 23 | 4 |
| 3-penten-2-one | 11 | 49 | 38 |
| 3-buten-2-one | 31 *61 in CK | 39 *51 in CK | 8 |
| 2,3-butanedione | 37 | 29 | −8 |
| 3-methyl-2-butanone | 8 | *82* | 74 |
| 3-methyl-2-pentanone | 8 | 9 | 1 |
| 2-methyl-3-pentanone | 1 | 9 | 8 |
| 4-methyl-2-pentanone | 0 | *64* | 64 |
| 6-methyl-5-hepten-2-one | 9 | 16 | 27 |
| 3-hydroxy-2-butanone | 11 | 35 | 24 |
| acetophenone | 9 | 46 | 37 |

TABLE 2-continued

Results of screening for compounds (high dose of 500 μL) with a mode of action similar to acetone are below. These compounds are also called "activators" or "activator 2" compounds where the number designation of activator denotes that those chemicals elicit different behaviors (e.g., probing, flight pattern) in attraction. Italicized numbers represent values or, when present, average values that capture greater than 50% of mosquitoes. (CK = check or control port):

| Compound/CLASS | Response (%) | Response with L-LA (%) | Δ[(Resp with LA)-Resp] (%) |
|---|---|---|---|
| CARBOXYLIC ACIDS: | | | |
| propanoic acid | 3 | 1 | −2 |
| ALCOHOLS: | | | |
| methanol | 10 | *66* | 56 |
| ethanol | 9 | *57* | 48 |
| p-cresol | 5 | 32 | 27 |
| 1-hepten-3-ol | 10 | 15 | 5 |
| HALOGENATED: | | | |
| methylene chloride | *87* | *70 90* | −7 |
| chloroform | 24 | *76* | 52 |
| carbon tetrachloride | *92* | *92* | 0 |
| bromoform | 27 | *64* | 37 |
| ALDEHYDES: | | | |
| formaldehyde (37%) | 1 | 5 | 4 |
| acetaldehyde | 8 | 29 | 21 |
| butyraldehyde | 6 | 7 | 1 |
| isobutyraldehyde | 13 | 32 | 19 |
| nonanal | 11 10 | 22 21 | 10 |
| benzaldehyde | 9 | 21 | 12 |
| ALKANES/ALKENES/HYDROCARBONS: | | | |
| isoprene | 12 | 23 | 11 |
| 1-heptene | 5 | 19 | 14 |
| 1-octene | 38 | 42 | 4 |
| 1-nonene | 6 | 8 | 2 |
| toluene | 7 | *59* | 52 |
| NITRILES: | | | |
| acetonitrile | 27 | *81* | 54 |
| benzonitrile | 4 | 48 | 42 |
| phenylacetonitrile | 16 | *63* | 47 |
| HETEROCYCLIC/FURANS: | | | |
| 2-methylfuran | 15 *30 in CK | 52 | 37 |
| SULFIDES: | | | |
| carbon disulfide | *82* | *89* | 7 |
| dimethyl sulfide | 32 | *79* | 47 |
| diethyl sulfide | 15 | *54* | 39 |
| ethyl vinyl sulfide | 18 | *55* | 37 |
| dimethyl disulfide | 36 | *86* | 50 |
| diethyl disulfide | 33 | 49 | 16 |
| methyl propyl disulfide | 19 | 40 | 21 |
| dimethyl trisulfide | 21 | *67* | 46 |
| dimethyl sulfoxide | 3 | 30 | 27 |
| ETHERS: | | | |
| diethyl ether | 25 | *56* | 31 |

Example 3

Table 3 illustrates the effectiveness of analogues of lactic acid as attractants for mosquitoes. In addition, Table 3 illustrates the synergistic effectiveness of these compounds with acetone as attractants for mosquitoes.

TABLE 3

Results of screening for compounds with a mode of action similar to lactic acid are below (also called "base" compounds for "base attractants"):

| Compound | Response (%) | Response with Ace (%) | Δ[(Resp with Ace) − Resp] (%) |
|---|---|---|---|
| L-lactic acid | 26 (see above) | 88 (see above) | 62 |
| D-lactic acid | 8 | 82 | 74 |
| glycolic acid | 17 | 81 81 | 64 |
| tartaric acid | 9 | 67 | 58 |
| thiolactic acid | 4 | 68 | 64 |
| 3-hydroxy-2-butanone | 9 | 57 | 48 |
| butanal | 6 | 7 | 1 |
| isoprene | 12 | 56 | 44 |
| 1-heptene | 4 | 34 | 30 |
| 1-octene | 38 | 63 | 25 |
| 1-nonene | 6 | 54 | 48 |

Ace = acetone

Example 4

Table 4 illustrates the effectiveness of humans for attracting *Aedes aegypti* mosquitoes. Data were collected from September 1997–June 1998.

TABLE 4

Human subjects tested in the olfactometer (raw data, % attraction):

| D. Kline | 72 83 74 85 78 81 68 86 | Avg: 78% |
|---|---|---|
| K. Posey | 70 67 55 79 78 | Avg: 70% |
| U. Bernier | 83 63 68 55 | Avg: 67% |

Example 5

Table 5 illustrates the effectiveness of several compositions as attractants for mosquitoes.

TABLE 5

Various mixtures and items examined, and described containers:

| | |
|---|---|
| 9-spot well plates with <10 μL pure L-LA + 500 μL acetone | 95% |
| LA + acetone (four 8.9 mm diam. caps) | 95% |
| Dish: LA + chloroform Cap: 90:10 | 95% |
| Dish: LA + CS₂ + chloroform; Cap to 20 ml scintillation vial: 90/10 | 94% |
| LA + acetone (two 8.9 mm diam. caps) | 94% |
| LA + acetone + 100 μL methylene chloride | 93% |
| LA + acetone + ethanol | 92% |
| LA + acetone (one 8.9 mm diam. cap) - max 400 μL acetone per cap | 92% |
| LA + 300 μL 1-octene + acetone | 92%, 89% |
| 500 μL acetone (dish 1) + 200 μg LA (dish 2) | 91% |
| 500 μL (75:25) + 200 μg LA | 90% |
| LA + acetone + 2-butanone | 89% |
| LA + acetone + 100 μL CS₂ | 89% |
| LA + isoprene (8.9 mm diam. cap) | 88% |
| LA + acetone + 50 μL 3-pentanone | 88% |
| 500 μL (90:10) acetone/dmds + 200 μg LA | 88% |
| 9-spot well plate with equal amounts of AM1 components + LA | 88% |
| LA + 75:25 + acetonitrile | 87% |
| Dish: LA + CS₂ Cap: 90:10 | 87% |
| 9-spot well plate with LA (wet) + acetone | 86% |
| 266 ng glycolic acid + 1 ml acetone | 86% |
| 500 μL AM1 + 200 μg LA | 85% |
| 9-spot well plates with LA (wet) + 2 wells acetone | 83% |
| LA + acetone + 100 μL butanone | 80% |
| 500 μL (50:50) + 200 μg LA | 79% |
| LA + acetone + 100 μL acetonitrile | 78% |
| 9-spot well plates with 10 μL thiolactic acid + 2 wells acetone | 73% |
| D. Kline 4-day old worn sock | 71% |
| LA + 2-octanone + acetone | 68% |
| 500 μL AM1 | 47% |
| 266 μg glycolic acid + LA dried 3 min | 45% |
| LA + 5-nonanone + acetone | 44% |
| Acetonitrile + tartaric acid | 41% |
| 500 μL (90% acetone + 10% dimethyl disulfide) | 35% |
| 500 μL (75:25) acetone/dmds | 33% |
| 500 μL (50:50) acetone/dmds | 24% |
| 1-hepten-3-ol | 7% |

90:10, 75:25, and 50:50 refer to the ratio of acetone to dimethyl disulfide in the mixture.
LA = lactic acid
The default treatment for LA is 200 μg and for other chemicals, it is 500 μl of the compound, unless specified otherwise.
The scintillation vial cap (1W) has an inner diameter of 13.5 mm. The black autosampler (1B) vial caps have an inner diameter of 8.9 mm and can hold approximately 400 μL of liquid.
AM1 = attractant mixture 1 is formulated as follows: 100 ml acetone, 700 μL butanone, 5 μL 3-methyl-2-butanone, 10 μL 2-pentanone, 300 μL carbon disulfide, 10 μL dimethyl sulfide, 10 μL dimethyl disulfide, and 500 μL acetonitrile.

Example 6

Table 6 illustrates the average values for the effectiveness of several compounds and combinations of compounds as attractants for *Aedes aegypti*. These data were obtained from formal screenings and formal randomized tests.

TABLE 6

Average Values for Compounds and Compositions Tested for Attraction of *Aedes aegypti*

W = White Cap, ~1200 uL volume, B = Black Cap, ~400 uL volume, but omission rate determined by exposed surface area, temperature, and chemical volatility. I = Insert, ~225 uL volume. Numerical Doses have Units of ug for solids or uL for liquids-- Numerical Entries without letter designation indicate experiments in a 60 mL glass petri dish. Doses without units are typically μg for bases and μL for activators. Crys denotes a solid with 500 μg-2 mg sample mess. Data compiled only from "formal" screen tests and experiments with randomized design.

| Base | Dose | Activator 1 | Dose | Activator 2 | Dose | Response Avg % | Number of Tests |
|---|---|---|---|---|---|---|---|
| LA | 600 | Acetone | 500 | | | 96.9% | |
| LA | 50W | Acetone | 1B | | | 96.4% | |
| LA | 20W | Acetone | 1B | | | 94.9% | |
| LA | 50W | Dimethyl Disulfide | 1W | | | 93.3% | |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area, temperature, and chemical volatility. I = Insert, ~225 uL volume. Numerical Doses have Units of ug for solids or uL for liquids-- Numerical Entries without letter designation indicate experiments in a 60 mL glass petri dish. Doses without units are typically μg for bases and μL for activators. Crys denotes a solid with 500 μg-2 mg sample mess. Data compiled only from "formal" screen tests and experiments with randomized design.

| Base | Dose | Activator 1 | Dose | Activator 2 | Dose | Response Avg % | Number of Tests |
|---|---|---|---|---|---|---|---|
| LA | 200W | 1,1,1-Trichloroethane | 4B | | | 92.5% | |
| LA | 200 | Carbon Tetrachloride | 500 | | | 92.0% | |
| LA | 400 | Acetone | 1000 | | | 91.8% | n = 3 |
| | | Carbon Tetrachloride | 500 | | | 91.5% | |
| LA | 600 | Acetone | 1000 | | | 91.1% | n = 2 |
| LA | 100W | Acetone | 1W | | | 91.0% | |
| LA | 50W | Methylene Chloride | 1I | | | 90.8% | |
| LA | 200 | Acetone | 500 | Nitrogen | 50 | 90.3% | |
| LA | 200W | Acetone | 500 | | | 90.2% | |
| LA | 200 | Acetone | 375 | Dimethyl Disulfide | 125 | 90.0% | |
| LA | 400 | Acetone | 500 | | | 89.5% | n = 3 |
| LA | 10W | Acetone | 1B | | | 89.4% | n = 2 |
| LA | support | Acetone | 1500 | | | 89.3% | n = 2 |
| LA | 200 | Acetone | 1W | | | 89.2% | |
| LA | 200 | Carbon Disulfide | 500 | | | 89.0% | |
| Glycolic Acid | crys | Acetone | 1B | | | 88.5% | |
| LA | 200 | Acetone | 450 | Dimethyl Disulfide | 50 | 88.0% | |
| LA | 100W | Acetone | 2B | | | 87.7% | |
| LA | 50 uL W | Acetone | 2B | Pyruvic Acid | 50 uL W | 87.7% | |
| LA | 200 | Acetone | 500 | | | 87.6% | n = 8 |
| LA | 10W | Acetone | 1W | | | 87.4% | |
| LA | 200W | Carbon Tetrachloride | 1B | | | 87.0% | |
| | | Methylene Chloride | 500 | | | 87.0% | |
| LA | 100W | Acetone | 4B | | | 86.6% | |
| LA | 50W | Dimethyl Disulfide | 1B | | | 86.6% | |
| LA | 50W | Methylene Chloride | 1W | | | 86.5% | |
| LA | 200W | Carbon Dioxide | 40 mL/min | | | 86.0% | n = 3 |
| LA | 2W | Acetone | 1W | | | 85.9% | |
| LA | 200 | Dimethyl Disulfide | 500 | | | 85.5% | |
| LA | 200W | Trichloroethylene | 4B | | | 85.5% | |
| LA | 400W | Acetone | 4B | | | 85.1% | |
| LA | 200 | AM1 | 500 | | | 85.0% | |
| LA | 200 | Acetone | 1000 | | | 84.9% | n = 26 |
| LA | 50W | Carbon Disulfide | 1B | | | 84.7% | |
| LA | 200W | Methylene Chloride | 4B | | | 83.7% | n = 3 |
| LA | 100W | Acetone | 1B | | | 83.3% | n = 2 |
| LA | 50W | Carbon Disulfide | 1W | | | 82.9% | |
| LA | 50W | Methylene Chloride | 1B | | | 82.7% | |
| D-LA | 200 | Acetone | 500 | | | 82.4% | |
| LA | 200 | 3-Methyl-2-Butanone | 500 | | | 82.0% | |
| LA | 200 | Acetone | 500 | Glycolic Acid | 266 | 82.0% | |
| | | Carbon Disulfide | 500 | | | 82.0% | |
| LA | 400W | Acetone | 2B | | | 81.6% | |
| LA | 2W | Methylene Chloride | 1W | | | 81.3% | |
| LA | 200W | Dimethoxymethane | 1B | | | 81.1% | |
| Glycolic Acid | 266 | Acetone | 500 | | | 81.0% | |
| LA | 200 | Acetonitrile | 500 | | | 81.0% | |
| LA | 200 | Butanone | 500 | | | 81.0% | |
| LA | 200W | Butanone | 2B | | | 80.7% | n = 3 |
| | | Methylene Chloride | 1W | | | 79.8% | n = 2 |
| Hand-L DK | | | | | | 79.5% | n = 5 |
| LA | 2W | Acetone | 1B | | | 79.2% | |
| LA | 200 | Acetone | 250 | Dimethyl Disulfide | 250 | 79.0% | |
| LA | 200 | Dimethyl suflide | 500 | | | 79.0% | |
| 3-Hydroxy-2-Butanone | 500 | Acetone | 500 | | | 78.0% | |
| LA | 200W | Acetone | 4B | | | 77.6% | n = 13 |
| LA | 200W | Methylene Chloride | 1B | | | 76.8% | n = 79 |
| LA | 200W | Trichloroacetonitrile | 1B | | | 76.8% | |
| LA | 50 uL W | Acetone | 4B | Pyruvic Acid | 50 uL W | 76.7% | |
| Hand-L KP | | | | | | 76.6% | n = 4 |
| LA | 200W | Chloroform | 1B | | | 76.3% | n = 4 |
| LA | 200W | Dimethyl Disulfide | 1W | | | 76.3% | n = 3 |
| LA | 200W | Isoprene | 4B | | | 76.3% | n = 3 |
| LA | 200W | Dimethyl Disulfide | 1B | | | 76.1% | n = 80 |
| LA | 200 | 2-Pentanone | 500 | | | 76.0% | |
| LA | 200 | Chloroform | 500 | | | 76.0% | |
| LA | 200W | Methylene Chloride | 1000 | | | 75.9% | n = 3 |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area,
temperature, and chemical volatility. I = Insert, ~225 uL volume. Numerical Doses have Units of ug for solids or uL for liquids--
Numerical Entries without letter designation indicate experiments in a 60 mL glass petri dish. Doses without units are typically µg
for bases and µL for activators. Crys denotes a solid with 500 µg-2 mg sample mess. Data compiled only from "formal" screen
tests and experiments with randomized design.

| Base | Dose | Activator 1 | Dose | Activator 2 | Dose | Response Avg % | Number of Tests |
|---|---|---|---|---|---|---|---|
| LA | 200W | Acetone | 1W | | | 75.0% | n = 108 |
| LA | 200W | Thiophene | 1B | | | 74.6% | |
| Hand-L UB | | | | | | 72.6% | n = 25 |
| LA | 200W | Tetrachloroethylene | 4B | | | 72.1% | |
| LA | 200W | Chloroform | 2B | | | 71.4% | n = 4 |
| LA | 200W | Chloroform | 4B | | | 70.7% | n = 3 |
| LA | 200 | Methylene Chloride | 500 | | | 70.0% | |
| LA | 200W | Acetone | 1B | | | 69.6% | n = 32 |
| LA | 400W | Acetone | 1B | | | 69.4% | |
| Hand-R KP | | | | | | 69.2% | n = 5 |
| LA | 200W | Acetone | 2B | | | 68.6% | n = 12 |
| LA | 200W | 2-Hexanone | 1B | | | 68.0% | |
| LA | 200W | Methylene Chloride | 2B | | | 68.0% | n = 3 |
| Thiolactic Acid | 100 uL | Acetone | 500 | | | 68.0% | |
| LA | 2W | Dimethyl Disulfide | 1W | | | 67.2% | |
| LA | 200 | Dimethyl Trisulfide | 500 | | | 67.0% | |
| Tartaric Acid | 180 | Acetone | 500 | | | 67.0% | |
| LA | 200W | Isoprene | 1B | | | 66.8% | n = 5 |
| LA | 200W | Butanone | 1B | | | 66.2% | n = 4 |
| LA | 200W | Butanone | 4B | | | 66.1% | n = 3 |
| LA | 200 | CO2 | 0.5 | mL/min Air | 50 mL/min | 66.0% | n = 2 |
| LA | 200 | MeOH | 500 | | | 66.0% | |
| LA | 50W | Acetone | 1I | Dimethyl Disulfide | 1I | 64.9% | |
| LA | 200W | Carbon Disulfide | 2B | | | 64.8% | n = 3 |
| LA | 200 | 4-Methyl-2-Pentanone | 500 | | | 64.0% | |
| LA | 200 | Bromoform | 500 | | | 64.0% | |
| LA | 200W | Acetone | 1I | Glycolic Acid | crys-W | 63.9% | |
| LA | 2W | Methylene Chloride | 1I | | | 63.5% | |
| LA | 50W | Acetone | 1I | | | 63.3% | |
| LA | | Phenylacetonitrile | 500 | | | 63.0% | |
| | | Acetone | 500 | 1-Octene | 500 | 63.0% | |
| LA | 200W | Dimethyl Disulfide | 2B | | | 62.3% | n = 3 |
| LA | 2W | Methylene Chloride | 1B | | | 62.3% | |
| LA | 50W | Dimethyl Disulfide | 1I | Carbon Disulfide | 1I | 61.4% | |
| LA | 2W | Acetone | 1I | | | 61.3% | |
| LA | 10W | Methylene Chloride | 1I | | | 61.2% | |
| LA | 200W | 1,1,2-Trichloroethane | 4B | | | 59.1% | |
| LA | 200 | Toluene | 500 | | | 59.0% | |
| | | Methylene Chloride | | | | 58.9% | |
| LA | 200W | Carbon Disulfide | 1B | | | 58.8% | n = 4 |
| LA | 200W | Isoprene | 1B | 2-Hexanone | 1B | 58.0% | |
| LA | 2W | Dimethyl Disulfide | 1I | | | 57.0% | |
| LA | 100W | Acetone | 1I | | | 56.8% | |
| Pyruvic Acid | 50 uL | Acetone | 4B | | | 56.7% | |
| | | Acetone | 500 | Nitrogen | 50 | 56.5% | |
| LA | 200W | Carbon Disulfide | 4B | | | 56.2% | n = 4 |
| LA | 200W | Acetone 90:10 | 1B | Dimethyl Disulfide 10:90 | 1B | 56.0% | |
| LA | 200 | Diethyl Ether | 500 | | | 56.0% | |
| | | Acetone | 500 | Isoprene | 500 | 56.0% | |
| | | Acetone | 500 | | | 55.8% | n = 3 |
| LA | 200 | Ethanol | 500 | | | 55.0% | |
| LA | 200 | Ethylvinyl Sulfide | 500 | | | 55.0% | |
| | | Methylene Chloride | 4B | | | 54.3% | n = 3 |
| LA | 50W | Acetone | 2I | | | 54.2% | |
| LA | 100W | | | | | 54.1% | |
| LA | 200 | Diethyl Sulfide | 500 | | | 54.0% | |
| LA | 50W | Acetone | 1I | Carbon Disulfide | 1I | 53.2% | |
| LA | 200W | Furfuryl Alcohol | 1B | | | 52.8% | |
| LA | 200W | Dimethyl Disulfide | 4B | | | 52.7% | n = 3 |
| | | Chloroform | 2B | | | 52.6% | n = 3 |
| LA | 200W | Phorone | 1B | | | 52.2% | |
| LA | 200 | 2-Methylfuran | 500 | | | 52.0% | |
| LA | 200W | 6-Methyl-5-Hepten-2-one | 1B | | | 52.0% | |
| LA | 200W | Acetone | 8I | | | 52.0% | |
| LA | 200 | 2-Hexanone | 500 | | | 51.0% | |
| LA | 200 | 3-Penten-2-one | 500 | | | 49.0% | |
| LA | 200 | Diethyl Disulfide | 500 | | | 49.0% | |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area, temperature, and chemical volatility. I = Insert, ~225 uL volume. Numerical Doses have Units of ug for solids or uL for liquids-- Numerical Entries without letter designation indicate experiments in a 60 mL glass petri dish. Doses without units are typically μg for bases and μL for activators. Crys denotes a solid with 500 μg-2 mg sample mess. Data compiled only from "formal" screen tests and experiments with randomized design.

| Base | Dose | Activator 1 | Dose | Activator 2 | Dose | Response Avg % | Number of Tests |
|---|---|---|---|---|---|---|---|
| LA | 200W | Acetone | 2I | | | 48.0% | |
| LA | 200 | Benzonitrile | 500 | | | 48.0% | |
| LA | 200 | 5-Nonanone | 500 | | | 47.0% | |
| LA | 200W | Acetone | 4I | | | 47.0% | n = 2 |
| | | AM1 | 500 | | | 47.0% | |
| LA | 200 | Acetophenone | 500 | | | 46.0% | |
| LA | 200 | Linalool | 500 | | | 46.0% | |
| | | Dimethyl Disulfide | 1W | | | 46.0% | n = 2 |
| | | Methylene Chloride | 2B | | | 46.0% | n = 3 |
| LA | 200W | 2,3-Butanedione | 1B | | | 45.8% | n = 4 |
| LA | 10W | Dimethyl Disulfide | 1I | | | 45.2% | |
| LA | 200W | Acetone | 1B | 2,3-Butanedione | 1B | 45.0% | |
| LA | 200 | Glycolic Acid | 266 | | | 45.0% | |
| LA | 200W | Dimethoxymethane | 1I | | | 44.4% | |
| LA | 200W | Methyl Butyrate | 1B | | | 43.1% | |
| LA | 200W | Acetone | 1I | | | 43.0% | |
| LA | 50W | Carbon Disulfide | 1I | | | 42.7% | |
| LA | 200 | 1-Octene | 500 | | | 42.0% | |
| LA | 200 | 2-Heptanone | 500 | | | 42.0% | |
| LA | 200W | Dimethyl Trisulfide | 1B | | | 41.0% | |
| Tartaric Acid | 180 | Acetonitrile | 500 | | | 41.0% | |
| LA | 200W | Isoprene | 2B | | | 40.5% | n = 4 |
| | | Chloroform | 4B | | | 40.2% | n = 3 |
| LA | 200W | 3-Buten-2-one | 1B | | | 40.0% | |
| LA | 200 | Methylpropyl Disulfide | 500 | | | 40.0% | |
| LA | 50W | Acetone | 3I | | | 39.1% | |
| DL-Mandelic Acid | crys | Acetone | 500 | | | 39.0% | |
| LA | 200 | 3-Buten-2-one | 500 | | | 39.0% | |
| LA | 200 | 3-Hexanone | 500 | | | 39.0% | |
| LA | 200W | 3-Pentanone | 1B | | | 39.0% | |
| | | Chloroform | 1B | | | 39.0% | n = 3 |
| | | Acetone | 4B | | | 38.3% | n = 8 |
| | | 1-Octene | 500 | | | 38.0% | |
| | | 2,3-Butanedione | 500 | | | 37.0% | |
| LA | 200W | 1-Methylpyrrole | 1B | | | 36.8% | |
| | | 2,3-Butanedione | 2B | | | 36.3% | n = 3 |
| | | Methylene Chloride | 1B | | | 36.3% | n = 79 |
| LA | 200 | 3-Heptanone | 500 | | | 36.0% | |
| LA | 200W | 3-Hexanone | 1B | | | 36.0% | |
| | | Dimethyl Disulfide | 500 | | | 36.0% | |
| LA | 10W | Acetone | 1I | | | 35.2% | n = 2 |
| LA | 200 | 3-Hydroxy-2-Butanone | 500 | | | 35.0% | |
| | | Acetone | 450 | Dimethyl Disulfide | 50 | 35.0% | |
| | | Acetone | 1W | | | 34.6% | n = 54 |
| LA | 2W | Dimethyl Disulfide | 1B | | | 33.8% | |
| | | Carbon Disulfide | 4B | | | 33.2% | n = 4 |
| | | Acetone | 375 | Dimethyl Disulfide | 125 | 33.0% | |
| | | Diethyl Disulfide | 500 | | | 33.0% | |
| LA | 200 | FC43 | 500 | | | 32.3% | |
| | | Butanone | 2B | | | 32.1% | n = 3 |
| LA | 200 | 4-Heptanone | 500 | | | 32.0% | |
| LA | 200 | Isobutanal | 500 | | | 32.0% | |
| LA | 200 | p-Cresol | 500 | | | 32.0% | |
| | | Dimethyl Sulfide | 500 | | | 32.0% | |
| | | Linalool | 500 | | | 32.0% | |
| LA | 200 | 1,1,3-Trichloroacetone | 500 | | | 31.7% | |
| | | 3-Buten-2-one | 500 | | | 31.0% | |
| Pyruvic Acid | 50 uL | | | | | 30.7% | |
| LA | 200 | Dimethylsulfoxide | 500 | | | 30.0% | |
| LA | 200 | 2,3-Butanedione | 500 | | | 29.0% | |
| LA | 200 | Acetaldehyde | 500 | | | 29.0% | |
| LA | 200W | Acetaldehyde | 1B | | | 29.0% | |
| LA | 200W | Acetonitrile | 4B | | | 29.0% | n = 3 |
| | | Dimethoxymethane | 1I | | | 29.0% | |
| | | 2,3-Butanedione | 1B | | | 28.7% | n = 3 |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area,
temperature, and chemical volatility. I = Insert, ~225 uL volume. Numerical Doses have Units of ug for solids or uL for liquids--
Numerical Entries without letter designation indicate experiments in a 60 mL glass petri dish. Doses without units are typically $\mu g$
for bases and $\mu L$ for activators. Crys denotes a solid with 500 $\mu g$-2 mg sample mess. Data compiled only from "formal" screen
tests and experiments with randomized design.

| Base | Dose | Activator 1 | Dose | Activator 2 | Dose | Response Avg % | Number of Tests |
|---|---|---|---|---|---|---|---|
| LA | 200 | 3-Pentanone | 500 | | | 28.0% | |
| | | Butanone | 500 | | | 28.0% | |
| | | Furfuryl Alcohol | 500 | | | 28.0% | |
| LA | 50W | Dimethyl Disulfide | 1I | | | 27.6% | |
| | | Acetone | 1B | | | 27.2% | n = 26 |
| LA | 200 | 6-Methyl-5-Hepten-2-one | 500 | | | 27.0% | |
| LA | 200 | | | | | 27.0% | n = 54 |
| | | Acetonitrile | 500 | | | 27.0% | |
| | | Bromoform | 500 | | | 27.0% | |
| | | Acetone | 2B | | | 26.9% | n = 6 |
| | | Methyl Butyrate | 500 | | | 26.8% | |
| | | Butanone | 4B | | | 25.9% | n = 3 |
| Glycolic Acid | crys-W | | | | | 25.3% | |
| LA | 200W | Acetonitrile | 2B | | | 25.0% | n = 3 |
| | | Diethyl Ether | 500 | | | 25.0% | |
| LA | 200W | 2,3-Butanedione | 2B | | | 24.0% | n = 3 |
| LA | 200 | 2-Decanone | 500 | | | 24.0% | |
| | | Acetone | 250 | Dimethyl Disulfide | 250 | 24.0% | |
| | | Chloroform | 500 | | | 24.0% | |
| Glycolic Acid | crys-W | Acetone | 1I | | | 23.8% | |
| LA | 200 | 1-Penten-3-one | 500 | | | 23.0% | |
| LA | 200 | Isoprene | 500 | | | 23.0% | |
| | | 2,3-Butanedione | 4B | | | 23.0% | n = 3 |
| Thiourea | crys | Acetone | 1W | | | 22.6% | |
| | | Dimethyl Disulfide | 1B | | | 22.4% | n = 80 |
| LA | 200W | 2,3-Butanedione | 4B | | | 22.0% | n = 3 |
| LA | 200 | Nonanal | 500 | | | 21.5% | n = 2 |
| | | Carbon Disulfide | 1B | | | 21.5% | n = 3 |
| | | Acetone | 1I | | | 21.4% | |
| LA | 200 | Benzaldehyde | 500 | | | 21.0% | |
| | | Dimethyl Trisulfide | 500 | | | 21.0% | |
| | | Dimethoxymethane | 1B | | | 20.3% | |
| Indole | 500 mg | Acetone | 500 | | | 20.0% | |
| LA | 200W | 3,4-Hexanedione | 4B | | | 20.0% | |
| LA | 200W | 3-Penten-2-one | 1B | | | 20.0% | |
| LA | 200 | 1-Heptene | 500 | | | 19.0% | |
| | | 1-Penten-3-one | 500 | | | 19.0% | |
| | | Methylpropyl Disulfide | 500 | | | 19.0% | |
| LA | 50 uL W | Pyruvic Acid | | 50 uL W | | 18.9% | |
| LA | 200W | Acetonitrile | 1B | | | 18.8% | n = 4 |
| | | Carbon Disulfide | 2B | | | 18.4% | n = 4 |
| D-LA | 200 | | | | | 18.1% | |
| | | Ethylvinyl Sulfide | 500 | | | 18.0% | |
| | | Methyl Butyrate | 1B | | | 17.1% | |
| Glycolic Acid | 266 | | | | | 17.0% | |
| LA | 200W | 2,3-Hexanedione | 4B | | | 17.0% | |
| | | 2-Heptanone | 500 | | | 17.0% | |
| | | 4-Heptanone | 500 | | | 17.0% | |
| | | Acetone | 500 | Propanoic acid | 500 | 17.0% | |
| LA | 2W | | | | | 16.8% | n = 3 |
| LA | 200W | 5-Methyl-2-Hexanone | 1B | | | 16.4% | |
| | | Dimethyl Disulfide | 4B | | | 16.3% | n = 3 |
| LA | 200W | | | Glycolic Acid | crys-W | 16.2% | |
| | | Isoprene | 2B | | | 16.1% | n = 3 |
| LA | 200 | 2-Octanone | 500 | | | 16.0% | |
| | | Phenylacetonitrile | 500 | | | 16.0% | |
| LA | 200W | | | | | 15.8% | n = 195 |
| | | 2-Methylfuran | 500 | | | 15.0% | |
| | | Diethyl Sulfide | 500 | | | 15.0% | |
| | | Dimethyl Disulfide | 2B | | | 14.7% | n = 3 |
| | | 2-Decanone | 500 | | | 14.0% | |
| | | 5-Nonanone | 500 | | | 14.0% | |
| | | Isoprene | 4B | | | 13.6% | n = 3 |
| 2-Amino-pyridine | 500 mg | Acetone | 500 | | | 13.2% | |
| LA | 200W | 1-Penten-3-one | 1B | | | 13.0% | |
| | | Isobutanal | 500 | | | 13.0% | |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area, temperature, and chemical volatility. I = Insert, ~225 uL volume. Numerical Doses have Units of ug for solids or uL for liquids-- Numerical Entries without letter designation indicate experiments in a 60 mL glass petri dish. Doses without units are typically $\mu$g for bases and $\mu$L for activators. Crys denotes a solid with 500 $\mu$g-2 mg sample mess. Data compiled only from "formal" screen tests and experiments with randomized design.

| Base | Dose | Activator 1 | Dose | Activator 2 | Dose | Response Avg % | Number of Tests |
|---|---|---|---|---|---|---|---|
| LA | 200 | 2-Nonanone | 500 | | | 12.0% | |
| LA | 200W | Isobutanal | 1B | | | 12.0% | |
| | | 3-Heptanone | 500 | | | 12.0% | |
| | | 3-Pentanone | 500 | | | 12.0% | |
| | | Isoprene | 500 | | | 12.0% | |
| | | Isoprene | 1B | | | 11.8% | n = 3 |
| 3-Hydroxy-2-Butanone | 500 | | | | | 11.0% | |
| | | 3-Penten-2-one | 500 | | | 11.0% | |
| | | Nonanal | 500 | | | 11.0% | |
| | | Methylene Chloride | 1I | | | 10.1% | |
| LA | 200W | 5-Methyl-3-hexen-2-one | 1B | | | 10.0% | |
| | | MeOH | 500 | | | 10.0% | |
| | | Nonanal | 500 | | | 10.0% | |
| DL-Malic Acid | crys | Acetone | 1W | | | 9.3% | |
| | | Butanone | 1B | | | 9.3% | n = 4 |
| LA | 200 | 2-Methyl-3-Pentanone | 500 | | | 9.0% | |
| LA | 200 | 3-Methyl-2-Pentanone | 500 | | | 9.0% | |
| LA | 200 | 3-Nonanone | 500 | | | 9.0% | |
| Tartaric Acid | 180 | | | | | 9.0% | |
| | | 6-Methyl-5-Hepten-2-one | 500 | | | 9.0% | |
| | | Acetophenone | 500 | | | 9.0% | |
| | | Benzaldehyde | 500 | | | 9.0% | |
| | | Ethanol | 500 | | | 9.0% | |
| | | Acetonitrile | 4B | | | 8.7% | n = 3 |
| | | 1,4-Diaminobutane | 1B | | | 8.6% | |
| LA | 200W | 6-Methyl-3,5-Heptadien-2-one | 1B | | | 8.2% | |
| | | Dimethyl Disulfide | 1I | | | 8.1% | |
| LA | 200 | 1-Nonene | 500 | | | 8.0% | |
| | | 2-Nonanone | 500 | | | 8.0% | |
| | | 2-Octanone | 500 | | | 8.0% | |
| | | 2-Pentanone | 500 | | | 8.0% | |
| | | 3-Methyl-2-Butanone | 500 | | | 8.0% | |
| | | 3-Methyl-2-Pentanone | 500 | | | 8.0% | |
| | | Acetaldehyde | 500 | | | 8.0% | |
| LA | 200 | Butanal | 500 | | | 7.0% | |
| | | Acetone | 500 | Butanal | 500 | 7.0% | |
| | | Toluene | 500 | | | 7.0% | |
| Succinic Acid | crys | Acetone | 1W | | | 6.9% | |
| LA | 200W | 4-Hexen-3-one | 1B | | | 6.7% | |
| | | 1-Nonene | 500 | | | 6.0% | |
| | | Butanal | 500 | | | 6.0% | |
| | | Furfuryl Alcohol | 1B | | | 5.4% | |
| LA | 200 | Formaldehyde | 500 | | | 5.0% | |
| | | 1-Heptene | 500 | | | 5.0% | |
| | | p-Cresol | 500 | | | 5.0% | |
| Glyoxylic Acid | 100 uL | Acetone | 1W | | | 4.9% | |
| LA | 200W | 1-Octen-3-one | 1B | | | 4.6% | |
| Thiolactic Acid | 100 uL | | | | | 4.0% | |
| | | 3-Nonanone | 500 | | | 4.0% | |
| | | Benzonitrile | 500 | | | 4.0% | |
| | | CO2 | 0.5 | | | 4.0% | |
| LA | 200W | 4-Decanone | 1B | | | 3.2% | |
| | | 2-Hexanone | 500 | | | 3.0% | |
| | | Dimethylsulfoxide | 500 | | | 3.0% | |
| | | Propanoic acid | 500 | | | 3.0% | |
| | | Acetone | 1I | | | 2.9% | |
| LA | 200W | 2-Methyl-3-Octanone | 1B | | | 2.5% | |
| | | Acetonitrile | 2B | | | 2.3% | n = 3 |
| LA | 200W | Diethyl Phthalate | 1B | | | 1.5% | |
| LA | 200W | 1,4-Diaminobutane | 1B | | | 1.4% | |
| LA | 200W | Butanal | 1B | | | 1.0% | |

TABLE 6-continued

Average Values for Compounds and Compositions
Tested for Attraction of *Aedes aegypti*
W = White Cap, ~1200 uL volume, B = Black Cap, ~400 uL volume, but omission rate determined by exposed surface area, temperature, and chemical volatility. I = Insert, ~225 uL volume. Numerical Doses have Units of ug for solids or uL for liquids--Numerical Entries without letter designation indicate experiments in a 60 mL glass petri dish. Doses without units are typically $\mu$g for bases and $\mu$L for activators. Crys denotes a solid with 500 $\mu$g-2 mg sample mess. Data compiled only from "formal" screen tests and experiments with randomized design.

| Base | Dose | Activator 1 | Dose | Activator 2 | Dose | Response Avg % | Number of Tests |
|---|---|---|---|---|---|---|---|
| LA | 200 | Propanoic acid | 500 | | | 1.0% | |
| | | 2-Methyl-3-Pentanone | 500 | | | 1.0% | |
| | | 3-Hexanone | 500 | | | 1.0% | |
| | | Acetonitrile | 1B | | | 1.0% | n = 3 |
| | | Formaldehyde | 500 | | | 1.0% | |
| LA | 200W | E-3-Nonen-2-one | 1B | | | 0.0% | |
| | | 4-Methyl-2-Pentanone | 500 | | | 0.0% | |

TABLE 7

Compounds and Compositions Tested for Attraction of *Aedes albopictus*

| Treatment | % caught |
|---|---|
| Glycolic Acid Crys./CO2 5 mL/min | 65.8 |
| DLK-R Sock, 1 day old | 64.4 |
| DLK-L Hand/CO2 (5 mL/min) | 60.6 |
| LA 200 $\mu$g/CO2 5 mL/min | 57.5 |
| DLK-L Hand | 55.6 |
| LA 200 $\mu$g/Glycolic Crys./CO2 5 mL/min | 50.6 |
| DLK-L Hand | 49.3 |
| DLK-L Hand | 45.8 |
| LA 200 $\mu$g/CO2 5 mL/min | 45.2 |
| LA 200 $\mu$g/CS2 1B/CO2 5 mL/min | 44.9 |
| LA 200 $\mu$g/CO2 5 mL/min | 42.7 |
| LA 200 $\mu$g/Acetone 1B/CO2 5 mL/min | 40.3 |
| LA 200 $\mu$g/DMDS 1B/CO2 5 mL/min | 36.9 |
| LA 200 $\mu$g/CC14 1B/CO2 5 mL/min | 35.1 |
| CO2 5 mL/min | 34.6 |
| LA 200 $\mu$g/CS2 500 $\mu$L Dish | 33.8 |
| LA 200 $\mu$g/Chloroform 1B | 33.8 |
| LA 200 $\mu$g/2,3-Butanedione 1B/MeC12 1B | 33.3 |
| LA 200 $\mu$g/MeC12 1B/CO2 5 mL/min | 32.9 |
| LA 200 $\mu$g/CC14 1B/MeC12 1B | 32.9 |
| CO2 5 mL/min | 32.0 |
| CO2 5 mL/min (water immersed) | 29.2 |
| DL-Mandelic Acid Crys./Thiophene 1B | 27.8 |
| LA 200 $\mu$g/2,3-Butanedione 500 1B | 27.6 |
| LA 200 $\mu$g/Thiophene 1B | 27.0 |
| Glycolic Acid Crys./Thiophene 1B | 26.8 |
| LA 200 $\mu$g/Acetone 1B/CO2 5 mL/min | 24.1 |
| CO2 5 mL/min | 23.0 |
| LA 200 $\mu$g/CS2 1B/MeC12 1B | 22.7 |
| LA 200 $\mu$g/CS2 1B/MeC12 1B | 22.2 |
| LA 200 $\mu$g/MeC12 500 $\mu$L Dish | 19.4 |
| LA 200 $\mu$g/DMDS 1B/CO2 5 mL/min | 16.2 |
| LA 200 $\mu$g/Thiophene 500 $\mu$L Dish | 15.7 |
| LA 200 $\mu$g/Acetophenone 1B | 15.1 |
| Mushrooms from DLK Yard | 13.7 |
| Garlic clove | 13.7 |
| LA 200 $\mu$g/Phenylacetonitrile 1B | 12.5 |
| LA 200 $\mu$g/Ethylvinyl Sulfide 1B | 12.5 |
| LA 200 $\mu$g/CS2 1B/2,3-Butanedione 1B | 12.0 |
| LA 200 $\mu$g/CC14 1B | 12.0 |
| LA 200 $\mu$g/Diethyl Sulfide 1B | 11.9 |
| LA 200 $\mu$g | 11.7 |
| LA 200 $\mu$g/Benzaldehyde 1B | 11.6 |
| LA 200 $\mu$g/Acetone 500 $\mu$L Dish | 11.1 |
| CO2 5 mL/min | 11.1 |
| LA 200 $\mu$g/Ethyl Acetate 1B | 10.8 |
| 3-Hydroxy-2-Butanone 1B/Thiophene 1B | 10.8 |
| Glyoxylic Acid 1 mL Dish/Thiophene 1B | 10.4 |
| CO2 5 mL/min (water immersed) | 9.7 |
| LA 200 $\mu$g/2,3-Butanedione 1B/CO2 5 mL/min | 9.5 |
| Acetone 500 $\mu$L Dish | 9.1 |
| CS2 500 $\mu$L Dish/MeC12 500 $\mu$L Dish | 8.9 |
| LA 200 $\mu$g | 8.3 |
| LA 200 $\mu$g/Isoprene 1B | 8.1 |
| LA 200 $\mu$g/2,3-Butanedione 500 $\mu$L Dish | 8.1 |
| Mixture F1 1B | 7.6 |
| LA 200 $\mu$g/Thiourea Crys. Dish | 7.6 |
| LA 200 $\mu$g/Benzonitrile 1B | 7.6 |
| LA 200 $\mu$g/CS2 1B | 7.1 |
| LA 200 $\mu$g/1,1,2-Trichloroethane 1B | 7.0 |
| Limburger Cheese (European) | 6.8 |
| LA 200 $\mu$g/1-Octen-3-ol 1B | 6.8 |
| DL-Malic Acid Crys./Thiophene 1B | 6.8 |
| CO2 5 mL/min | 6.8 |
| 1,4-Diaminobutane 1B | 6.8 |
| LA 200 $\mu$g/Nitromethane 1B | 6.6 |
| LA 200 $\mu$g/Pyrazine 1B | 6.4 |
| LA 200 $\mu$g/2-Nonanone 1B | 6.4 |
| LA 200 $\mu$g/3-Nonanone 1B | 6.3 |
| LA 200 $\mu$g/2-Hexanone 1B | 6.3 |
| LA 200 $\mu$g/4-Hexen-3-one 1B | 5.5 |
| Mixture F2 1B/Butanal 1B/CS2 1B | 5.3 |
| LA 200 $\mu$g/Methylbutyrate 1B | 5.3 |
| Mixture F2 1B/Butanol 1B/CS2 1B | 5.1 |
| LA 200 $\mu$g/CS2 1B/DMDS 1B/Acet 1B | 4.7 |
| LA 200 $\mu$g/1-Butanol 1B | 4.6 |
| Pyruvic 1B/Thiophene 1B | 4.5 |
| LA 200 $\mu$g/2-Methylfuran 1B | 4.2 |
| LA 200 $\mu$g/2,3-Hexanedione 1B | 4.2 |
| LA 200 $\mu$g/1-Nonanal 1B | 4.2 |
| LA 200 $\mu$g/Nonanal 500 $\mu$L Dish | 4.1 |
| LA 200 $\mu$g/3-Methyl-2-Pentaone 1B | 3.9 |
| LA 200 $\mu$g/2-Pentanone 1B | 3.9 |
| LA 200 $\mu$g/2-Decanone 1B | 3.8 |
| LA 200 $\mu$g/4-Heptanone 1B | 3.7 |
| LA 200 $\mu$g/1-Methylpiperazine 1B | 3.7 |
| LA 200 $\mu$g/CS2 1B/DMDS 1B | 3.5 |
| LA 200 $\mu$g/50:50 Acetone:DMDS 1B | 2.7 |
| LA 200 $\mu$g/3-Methyl-2-Butanone 1B | 2.7 |
| LA 200 $\mu$g/3-Buten-2-one 1B | 2.7 |
| LA 200 $\mu$g/2-Octanone 1B | 2.7 |
| LA 200 $\mu$g/Diethyl Disulfide 1B | 2.6 |
| LA 200 $\mu$g/Acetonitrile 1B | 2.6 |
| LA 200 $\mu$g/6-Methyl-5-Hepten-2-One 1B | 2.6 |
| LA 200 $\mu$g/DMDS 500 $\mu$L Dish | 2.4 |
| LA 200 $\mu$g/Toluene 1B | 1.5 |
| LA 200 $\mu$g/Methylpropyl Disulfide 1B | 1.4 |
| LA 200 $\mu$g/3-Heptanone 1B | 1.4 |
| LA 200 $\mu$g/2-Methyl-3-Pentanone 1B | 1.4 |
| LA 200 $\mu$g/2-Heptanone 1B | 1.4 |

TABLE 7-continued

Compounds and Compositions Tested for Attraction of *Aedes albopictus*

| Treatment | % caught |
|---|---|
| LA 200 μg/2,4-Pentanedione 1B | 1.4 |
| CO2 5mL/min (water immersed) | 1.4 |
| LA 200 μg/Butanal 1B | 1.3 |
| LA 200 μg/5-Nonanone 1B | 1.3 |
| LA 200 μg/1-Hexen-3-ol 1B | 1.3 |
| LA 200 μg/1,4-Diaminobutane | 1.3 |
| LA 200 μg/Thiolactic Acid 1B | 0.0 |
| LA 200 μg/3,4-Hexanedione 1B | 0.0 |

Key to abbreviations in Table:
LA = L-Lactic Acid, CS2 = Carbon Disulfide, MeCl2 = Methylene Chloride = Dichoromethane, DMDS = Dimethyl Disulfide, CCl4 = Carbon Tetrachloride, Crys. = Crystalline Solid, 1B = 1 Black cap of approx. 400 mL volume, DLK = Dan Kline, -L = left hand or left sock, -R = right hand or right sock

TABLE 8

Compounds and Compositions Tested for Attraction of *Anopheles albimanus*

| Treatment | % caught |
|---|---|
| LA 200 μg/MeC12 500 μL dish | 97.4 |
| DMDS 500 μL | 97.3 |
| LA 200 μg/DMDS 500 μL dish | 92.5 |
| LA 200 μg/MeC12 1B | 92.0 |
| Dimethyl Trisulfide 500 μL | 91.8 |
| LA 200 μg/Acetone 500 μL dish | 91.7 |
| LA 200 μg/Acetone 500 μL dish | 89.9 |
| LA 200 μg/Acetone 500 μL dish | 83.0 |
| 4-Hexen-3-one 500 μL | 79.2 |
| Chloroform 500 μL | 78.7 |
| LA 200 μg/MeC12 1B | 77.6 |
| MeC12 500 μL | 75.7 |
| CC14 500 μL | 74.0 |
| Dimethyl Sulfide 500 μL | 68.4 |
| Thiophene 500 μL | 68.0 |
| Trichloroacetonitrile 500 μL | 65.3 |
| 1,1,2-Trichloroethane 500 μL | 64.4 |
| MeC12 1B | 64.4 |
| MeC12 1B | 63.0 |
| LA 200 μg/Thiophene 1B | 62.7 |
| 1,1,1-Trichloroethane 500 μL | 61.0 |
| LA 200 μg/MeC12 1B | 58.7 |
| Trichloroethylene 500 μL | 57.9 |
| LA 200 μg/Acetone 500 μL dish | 57.0 |
| CS2 500 μL | 56.0 |
| Methylbutyrate 500 μL | 55.8 |
| 3-Pentanone 500 μL | 53.9 |
| Phorone 500 μL | 50.6 |
| DMDS 1B | 49.3 |
| LA 200 μg/MeC12 1B | 48.6 |
| Butanone 500 μL | 47.9 |
| Furfuryl Alcohol 500 μL | 46.7 |
| 3-Buten-2-one 500 μL | 45.2 |
| LA 200 μg/DMDS 1B | 44.7 |
| LA 200 μg/CS2 1B | 42.7 |
| Ethanethiol 500 μL | 40.0 |
| LA 200 μg/Chloroform 1B | 39.5 |
| DMDS 1B/Thiophene 1B | 37.8 |
| 2-Methylfuran 500 μL | 35.5 |
| Benzaldehyde 500 μL | 35.5 |
| 2-Methyl-3-Heptanone 500 μL | 34.7 |
| Diethyl Sulfide 500 μL | 33.3 |
| LA 200 μg/Dimethyl Sulfide 1B | 32.4 |
| LA 200 μg/CC14 1B | 32.0 |
| DMDS 1B | 31.5 |
| 2-Methyl-3-Octanone 500 μL | 30.1 |
| Acetone 500 μL | 29.6 |
| p-Cresol 500 μL | 29.5 |
| 1-Penten-3-one 500 μL | 29.3 |
| Pyrazine 500 μL | 29.3 |

TABLE 8-continued

Compounds and Compositions Tested for Attraction of *Anopheles albimanus*

| Treatment | % caught |
|---|---|
| 2-Octanone 500 μL | 28.6 |
| Ethyl Acetate 500 μL | 28.4 |
| Mesityl Oxide 500 μL | 28.4 |
| DMDS 1B | 28.0 |
| DMDS 1B | 27.4 |
| 2-Nonanone 500 μL | 27.0 |
| LA 200 μg/DMDS 1B | 26.9 |
| F1 Mixture 500 μL | 26.4 |
| 6-Methyl-5-Hepten-2-one 500 μL | 26.0 |
| Butanone 1B/Thiophene 1B | 26.0 |
| Ethylvinyl Sulfide 500 μL | 25.4 |
| 3-Octanone 500 μL | 25.0 |
| 3-Methyl-2-Butanone 500 μL | 24.4 |
| 1-Octen-3-ol 500 μL | 24.0 |
| 1-Propanethiol 500 μL | 24.0 |
| Butanone 1B/DMDS 1B | 22.7 |
| Nitromethane 500 μL | 22.1 |
| LA 200 μg/5-Nonanone 1B | 21.1 |
| 2-Thiopropane 500 μL | 20.5 |
| DMDS 1B | 20.5 |
| 2,4-Pentanedione 500 μL | 19.4 |
| 2,6-Dimethyl-4-Heptanone 500 μL | 18.7 |
| 6-Methyl-3,5-Heptadien-2-one 500 μL | 18.7 |
| 3,4-Hexanedione 1B/Methylbutyrate 1B | 17.9 |
| Nitromethane 500 μL | 17.3 |
| Tetrachloroethylene 500 μL | 17.3 |
| 3-Methyl-2-Pentanone 500 μL | 17.1 |
| LA 200 μg/3-Buten-2-one 1B | 17.1 |
| LA 200 μg/Butanone 1B | 16.0 |
| 3-Nonanone 500 μL | 15.8 |
| LA 200 μg/2-Thiopropane 1B | 15.8 |
| LA 200 μg/4-Hexen-3-one 1B | 14.7 |
| Toluene 500 μL | 13.5 |
| Isophorone 500 μL | 13.3 |
| LA 200 μg/Acetone 1B | 13.3 |
| LA 200 μg/2-Methylfuran 1B | 13.0 |
| 5-Nonanone 500 μL | 12.7 |
| Methylpropyl Disulfide 500 μL | 12.3 |
| Acetone 1B | 12.2 |
| 4-Hexen-3-one 1B/Thiophene 1B | 12.0 |
| LA 200 μg/1-Methylpyrrole 1B | 12.0 |
| LA 200 μg/p-Cresol 1B | 12.0 |
| 5-Methyl-3-Hexen-2-one 500 μL | 11.8 |
| 5-Methyl-2-Hexanone 500 μL | 11.7 |
| 3-Heptanone 500 μL | 11.3 |
| 2-Pentanone 500 μL | 10.8 |
| 1-Methylpyrrole 500 μL | 10.7 |
| 5-Methyl-3-Hexen-2-one 500 μL | 10.7 |
| Acetone 1B | 10.7 |
| DMDS 1B/4-Hexen-3-one 1B | 10.7 |
| t-3-Nonen-2-one 500 μL | 10.7 |
| 3,4-Hexanedione 500 μL | 10.5 |
| 2-Heptanone 500 μL | 10.4 |
| LA 200 μg/Acetone 1B | 10.4 |
| 3-Decanone 500 μL | 9.3 |
| LA 200 μg/Acetone 1B | 9.3 |
| LA 200 μg/3-Nonanone 1B | 9.2 |
| LA 200 μg/Acetone 1B | 9.1 |
| 2,4-Pentanedione 500 μL | 9.0 |
| LA 200 μg/Benzonitrile 1B | 8.9 |
| 3-Hexanone 500 μL | 8.3 |
| Butanone 1B/4-Hexen-3-one 1B | 8.1 |
| LA 200 μg/2-Decanone 1B | 8.1 |
| 4-Heptanone 500 μL | 8.0 |
| Acetophenone 500 μL | 7.9 |
| LA 200 μg/Benzaldehyde 1B | 7.9 |
| 4-Decanone 500 μL | 7.8 |
| LA 200 μg/2-Nonanone 1B | 6.7 |
| Methyl Urea Crys dish | 6.5 |
| 1,1,3-Trichloroacetone 500 μL | 5.6 |
| 2-Methyl-3-Pentanone 500 μL | 5.3 |
| LA 200 μg/2-Heptanone 1B | 5.3 |
| LA 200 μg/Ethyl Acetate 1B | 5.3 |
| Methylbutyrate 1B/5-Methyl-3-Hexen-2-one 1B | 5.3 |

TABLE 8-continued

Compounds and Compositions Tested for Attraction of *Anopheles albimanus*

| Treatment | % caught |
|---|---|
| DMDS 1B | 5.2 |
| 2-Hexanone 500 µL | 4.3 |
| 2-Undecanone 500 µL | 4.2 |
| 1-Nonanol 500 µL | 4.1 |
| LA 200 µg/Ethylvinyl Sulfide 1B | 4.1 |
| 2-Decanone 500 µL | 4.0 |
| LA 200 µg/2-Pentanone 1B | 4.0 |
| LA 200 µg/3-Pentanone 1B | 4.0 |
| LA 200 µg/Acetone 1B | 4.0 |
| LA 200 µg/Acetophenone 1B | 4.0 |
| LA 200 µg/Allyl Disulfide 1B | 4.0 |
| Methylbutyrate 1B/Furfuryl Alchohol 1B | 4.0 |
| 6-Undecanone 500 µL | 3.9 |
| LA 200 µg/3-Heptanone 1B | 3.9 |
| Benzonitrile 500 µL | 3.8 |
| LA 200 µg/2-Octanone 1B | 3.8 |
| Diethyl Disulfide 500 µL | 2.8 |
| 2,3-Hexanedione 500 µL | 2.7 |
| Acetic Acid 500 µL | 2.7 |
| LA 200 µg/4-Heptanone 1B | 2.7 |
| LA 200 µg/Diethyl Sulfide 1B | 2.7 |
| LA 200 µg/DMSO 1B | 2.7 |
| Pentane 500 µL | 2.7 |
| Thiourea Crys dish | 2.7 |
| 1-Tetradecene 500 µL | 1.4 |
| 2,3-Butanedione 500 µL | 1.4 |
| 2-Dodecanone 500 µL | 1.4 |
| 3,4-Hexanedione 500 µL | 1.4 |
| LA 200 µg | 1.4 |
| LA 200 µg/4-Methyl-2-Pentanone 1B | 1.4 |
| Pyruvic Acid 500 µL | 1.4 |
| 1-Methylpiperazine 500 µL | 1.3 |
| 2-Tridecanone 500 µL | 1.3 |
| 3-Hydroxy-2-Butanone 500 µL | 1.3 |
| 4-Methyl-2-Pentanone 500 µL | 1.3 |
| Butanal 500 µL | 1.3 |
| Glutaric Acid Crys dish | 1.3 |
| Glycolic Acid Crys dish | 1.3 |
| Glyoxylic Acid 500 µL | 1.3 |
| Indole 500 µL | 1.3 |
| LA 200 µg | 1.3 |
| LA 200 µg/3-Hydroxy-2-Butanone 1B | 1.3 |
| LA 200 µg/Diethyl Disulfide 1B | 1.3 |
| LA 200 µg/Methylpropyl Disulfide 1B | 1.3 |
| LA 400 µg dish | 1.3 |
| Lauric Acid 500 µL | 1.3 |
| Phenylacetonitrile 500 µL | 1.3 |
| 2-Aminopyridine 500 µL | 0.0 |
| Acetonylacetone 500 µL | 0.0 |
| Allyl Disulfide 500 µL | 0.0 |
| DL-Malic Acid Crys dish | 0.0 |
| DL-Mandelic Acid Crys dish | 0.0 |
| DMSO 500 µL | 0.0 |
| Formic Acid 500 µL | 0.0 |
| Isoprene 500 µL | 0.0 |
| LA 200 µg | 0.0 |
| LA 200 µg/2-Hexanone 1B | 0.0 |
| LA 200 µg/2-Methyl-3-Pentanone 1B | 0.0 |
| LA 200 µg/3-Hexanone 1B | 0.0 |
| LA 200 µg/3-Methyl-2-Butanone 1B | 0.0 |
| LA 200 µg/3-Methyl-2-Pentanone 1B | 0.0 |
| LA 200 µg/Phenylacetonitrile 1B | 0.0 |
| LA 200 µg/Toluene 1B | 0.0 |
| Succinic Acid Crys dish | 0.0 |
| Thiolactic Acid 500 µL | 0.0 |

Example 9

TABLE 9

Formulation and Verification of the Best Blend
(Note: ~10:1 Acetone:DMDS emission rate)

| | | |
|---|---|---|
| 200 µg L-lactic acid (1w) | 8% vs. 200 µg L-lactic acid (1w) + Acetone (3B) | 61% |
| Acetone (3B) | 12% vs. 200 µg L-lactic acid (1w) + Acetone (3B) | 59% |
| 200 µg L-lactic acid (1w) + Acetone (3B) | 28% vs. 200 µg L-lactic acid (1w) + Acetone (3B) + DMDS (1B) | 47% |
| 200 µg L-lactic acid (1w) + Acetone (B) | 42% vs. 200 µg L-lactic acid (1w) + Acetone (1B) + DMDS (1I) | 54%* |

*Notes:
overall, 95.2% mosquitoes trapped, ~30 µL in DMDS (dimethyl disulfide) insert, giving emission of ~100:1 Acetone:DMDS.

Example 10

TABLE 10

Types of Traps

Bed nets
Bates type stable traps
Cylindrical lard can traps
No. 10 Trinidad trap
Trueman & McIver ramp trap
Plexiglas trap
Kato's dry ice trap
DeFoliant & Morris conical trap
Malaise trap
Carbon dioxide light traps
Fay-Prince carbon dioxide trap
Sticky trap
New Jersey light trap
ACIS trap (Army Collapsible Insect Surveillance)
CDC light trap
Kimsey & Chaniotis trap
EVS light trap
Monk's Wood light trap
U.S. Army solid state light trap (AMSS)
Pfuntner light trap
Star beam sticky light trap
Cylindrical light trap
Updraft light traps
"Nozawa" trap
"AS" trap
UV light trap
Flashing light trap
Non-electrical light trap
Haufe & Burgess trap
Fay-Prince trap
Wilton & Kloter cylinder trap
Duplex cone trap
Ikeshoji cylinder sound trap
Ikeshoji & Ogawa cup trap
Kanda et al. cylinder and lantern traps
Heat traps
Sugar-base attraction traps The synergistic attractant compositions of the present invention may be provided by any number of mechanisms and in different formats appropriate to particular types of usage. The main function of the formats and mechanisms is to provide release of the attractant over a period of time sufficient to attract arthropods (e.g., mosquitoes) effectively, and especially to attract arthropods effectively to an available source of arthropod control material (e.g., insecticide, pheromone, microbial agent) which is effective against mosquitoes, and the like, as described above.

The compositions of the present invention may or may not comprise carbon dioxide. In the embodiment of the present invention wherein the composition does not comprise carbon dioxide, an additional benefit of the present invention is attained. In such an embodiment, highly-efficient, attractive blends for arthropod traps that do not require carbon dioxide are obtained.

An additional benefit of the compositions of the present invention include the obviation for live baits.

The mechanisms and formats will, of course, vary among the various compositions depending on the volatility, persistence, aerial stability, moisture sensitivity, and the like of the individual ingredients and compositions. Moisture, heat and light may optionally be added to the compounds of the present invention to enhance efficiency. The structures used to release the attractant compositions of the present invention could be as simple as a tray carrying the composition, a housed tray or other container carrying the compositions, timed release canisters or spray cans, absorbent materials retarding the release of the attractant (e.g., fabric, paper, porous material, foam, absorbent polymer, super absorbent polymer [e.g., the super absorbent acrylic polymers as described in U.S. Pat. No. 5,679,364], containers with semipermeable membranes, vented containers, and the like). The materials which would more actively attack the arthropods may be associated with the attractant (in a mixture) or may be located near the attractants so the chemicals do not adversely interact or react.

In addition, combining the compositions of the present invention with an insecticide provides a means of local extermination, not requiring wide-disbursement of the insecticide. Addition of a slow release chemical mechanism, such as paraffin, or other suitable viscous chemical (e.g., glycerol) provides a means to reduce the evaporation rates of the compositions.

What is claimed is:

1. A composition comprising mosquito attracting amounts of lactic acid and carbon disulfide.

2. A composition consisting of mosquito attracting amounts of lactic acid and butanone.

3. A composition consisting of mosquito attracting amounts of lactic acid and 2-pentanone.

4. A composition consisting essentially of mosquito attracting amounts of lactic acid and carbon disulfide.

5. A composition consisting essentially of mosquito attracting amounts of lactic acid, carbon disulfide, and carbon dioxide.

6. A method for attracting mosquitos comprising exposing an environment with a composition consisting of mosquitoes attracting amounts of lactic acid and 2-pentanone.

7. A method for attracting mosquitoes comprising exposing an environment with a composition consisting essentially of mosquito attracting amounts of lactic acid and carbon disulfide.

8. A method for attracting mosquitoes comprising exposing an environment with a composition consisting essentially of mosquito attracting amounts of lactic acid, carbon disulfide, and carbon dioxide.

9. A method for attracting mosquitoes comprising exposing an environment with a composition consisting of mosquito attracting amounts of lactic acid and acetone.

10. A method for attracting mosquitoes comprising exposing an environment with a composition consisting of mosquito attracting amounts of pyruvic acid and acetone.

11. A method for attracting mosquitoes comprising exposing an environment with a composition consisting of mosquito attracting amounts of glycolic acid and acetone.

12. A method for attracting mosquitoes comprising exposing an environment with a composition comprising of mosquito attracting amounts of lactic acid, carbon disulfide, and carbon dioxide.

* * * * *